US009173934B2

(12) United States Patent
Valenta et al.

(10) Patent No.: US 9,173,934 B2
(45) Date of Patent: Nov. 3, 2015

(54) WHEAT ALLERGENS

(75) Inventors: Rudolf Valenta, Theresienfeld (AT); Claudia Constantin, Vienna (AT); Santiago Quirce, Madrid (ES)

(73) Assignee: Phadia AB, Uppsala (SE)

( * ) Notice: Subject to any disclaimer, the term of this patent is extended or adjusted under 35 U.S.C. 154(b) by 296 days.

(21) Appl. No.: 12/744,885

(22) PCT Filed: Nov. 28, 2008

(86) PCT No.: PCT/SE2008/051377
§ 371 (c)(1),
(2), (4) Date: Aug. 11, 2010

(87) PCT Pub. No.: WO2009/070118
PCT Pub. Date: Jun. 4, 2009

(65) Prior Publication Data
US 2010/0305049 A1 Dec. 2, 2010

Related U.S. Application Data

(60) Provisional application No. 60/991,338, filed on Nov. 30, 2007.

(30) Foreign Application Priority Data

Nov. 30, 2007 (SE) ...................... 0702680

(51) Int. Cl.
| A61K 39/00 | (2006.01) |
| A61K 39/35 | (2006.01) |
| A61K 39/38 | (2006.01) |
| C07K 1/00 | (2006.01) |
| C07K 14/00 | (2006.01) |
| C07K 17/00 | (2006.01) |
| A61K 39/36 | (2006.01) |
| C07K 14/415 | (2006.01) |
| G01N 33/68 | (2006.01) |

(52) U.S. Cl.
CPC .......... *A61K 39/35* (2013.01); *A61K 39/36* (2013.01); *C07K 14/415* (2013.01); *G01N 33/6854* (2013.01)

(58) Field of Classification Search
None
See application file for complete search history.

(56) References Cited

U.S. PATENT DOCUMENTS

| 7,214,786 | B2 | 5/2007 | Kovalic et al. | |
| 7,569,389 | B2 * | 8/2009 | Feldmann et al. | 435/468 |
| 2005/0108791 | A1 * | 5/2005 | Edgerton | 800/284 |
| 2006/0048240 | A1 * | 3/2006 | Alexandrov et al. | 800/278 |
| 2006/0107345 | A1 * | 5/2006 | Alexandrov et al. | 800/278 |
| 2007/0039067 | A1 * | 2/2007 | Feldmann et al. | 800/278 |
| 2007/0044171 | A1 * | 2/2007 | Kovalic et al. | 800/278 |
| 2007/0275427 | A1 | 11/2007 | Akimoto et al. | |
| 2010/0083407 | A1 * | 4/2010 | Feldmann et al. | 800/298 |

FOREIGN PATENT DOCUMENTS

| CN | 1930474 A | 3/2005 |
| EP | 1586652 A1 | 10/2005 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*
Lazar et al. 'Transforming Growth Factor alpha:Mutation of Aspartic Acid 47 and Leucine 48 Results in Different Biological Activities.' Mol. Cell. Biol. 8(3):1247-1252, 1988.*
Blumenthal et al. 'Definition of an Allergen.' Allergens and Allergen Immunotherapy. Ed. R Lockey, S. Bukantz and J. Bousquet. New York: Marcel Decker, 2004. 37-50.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473, 2000.*
Kim et al. 'Protein immobilization techniques for microfluidic assays.' Biomicrofluidics 7, 041501,2013.*
Goel et al. http://www.rpi.edu/dept/chem-eng/Biotech-Environ/IM-MOB/goel2nd.html., 1994.*
Mittag et al, "Immunoglobulin E-reactivity of Wheat-Allergic Subjects (baker's asthma, food allergy, wheat-dependent, exercise-induced anaphylaxis) to Wheat Protein Fractions with Different Solubility and Digestibility," Molecular Nutrition & Food Research, vol. 48, pp. 380-389, 2004.
Di Gennaro et al, "cDNA Closing and Heterologous Expression of a Wheat Proteinase Inhibitor of Subtilisin and Chymotrysin (WSCI) that Interferes with Digestive Enzymes of Insect Pests," Biological Chemistry, vol. 386, pp. 383-389, Apr. 2005.

(Continued)

Primary Examiner — Nora Rooney
(74) Attorney, Agent, or Firm — Porter Wright Morris & Arthur LLP

(57) ABSTRACT

The present invention relates to the field of IgE-mediated allergy, particularly occupational asthma such as bakers asthma. More specifically the invention relates to the identification of a novel wheat allergen and the use thereof in therapy and diagnosis of IgE-mediated allergy. Furthermore the present invention provides the use of known peptides and proteins in therapy and diagnosis. The invention also relates to methods for diagnosis and treatment of IgE-mediated allergy in mammals.

3 Claims, 12 Drawing Sheets

(56) References Cited

OTHER PUBLICATIONS

Figure 2:
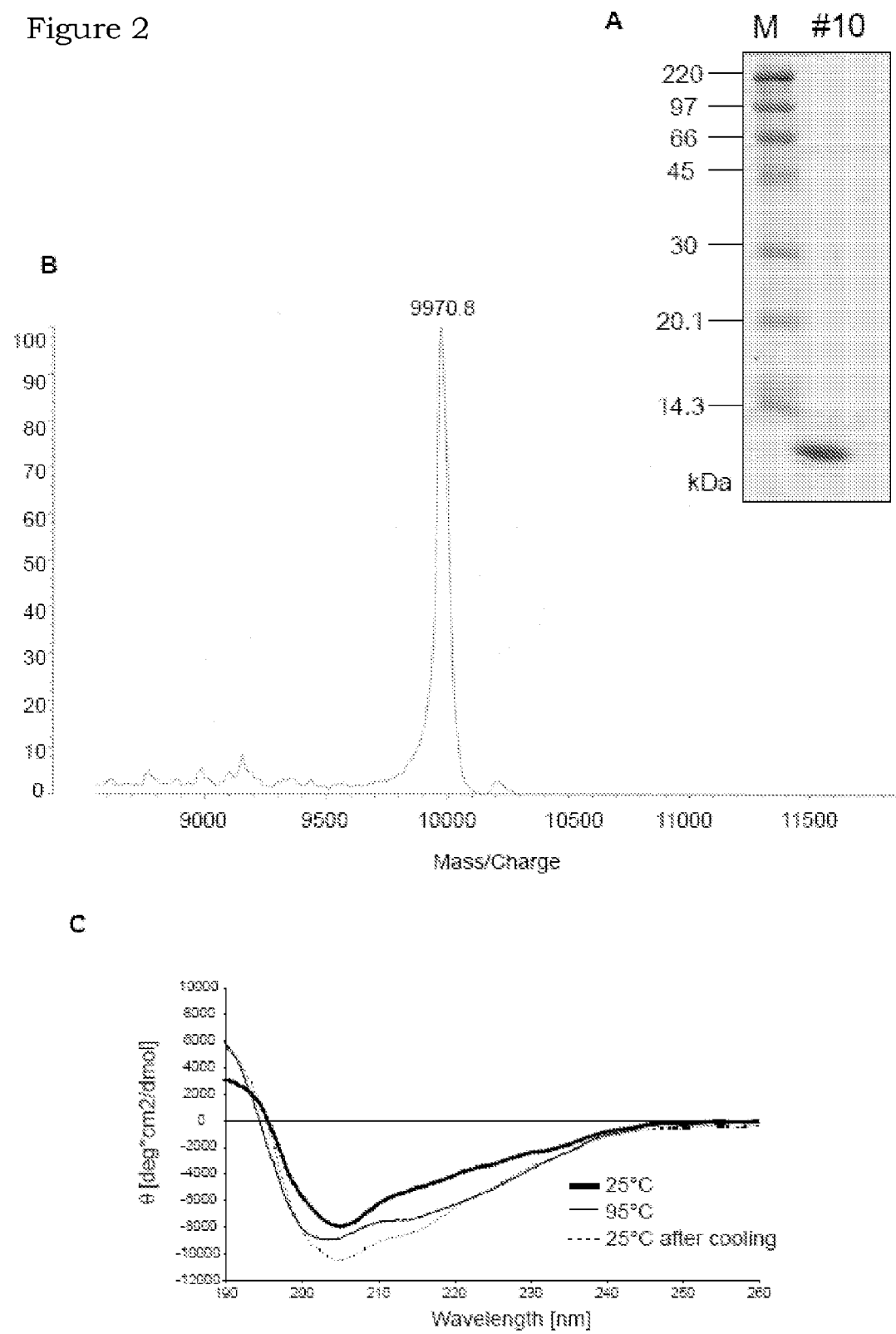

Weichel et al, "Wheat and Maize Thioredoxins: A Novel Cross-Reactive Cereal Allergen Family Related to Baker's Asthma," Journal of Allergy and Clinical Immunology, vol. 117, No. 3, pp. 676-681, Mar. 2006, (online Jan. 20, 2006).
Database UNIPROT (Online), Accession No. Q6W8Q2, May 1, 2007.
Garvey et al, IgE-mediated allergy to chlorhexidine, Journal of Allergy and Clinical Immunology, 2007, vol. 120, No. 2, p. 409-415, Online Jun. 13, 2007.
Palacin et al, Wheat lipid transfer protein is a major allergen associated with baker's asthma, Journal of Allergy and Clinical Immunology, 2007, vol. 120, No. 5, p. 1132-1138, Online Aug. 23, 2007.
Salcedo et al, Wheat Allergens Associated with Baker's Asthma, Journal of Investigational Allergology and Clinical Immunology, 2011, vol. 21, No. 2, p. 81-92.
Konarev et al, The distribution of serine proteinase inhibitors in seeds of the Asteridae, Phytochemistry, 2004, vol. 65, No. 22, p. 3003-3020.
Constantin et al, Molecular and Immunological Characterization of a Wheat Serine Proteinase Inhibitor as a Novel Allergen in Baker's Asthma, Journal of Immunology, Jun. 1, 2008, vol. 180, No. 11, p. 7451-7460.
Midoro-Horiuti et al, Pathogenesis-related proteins of plants as allergens, Annals of Allergy, Asthma & Immunology, 2001, vol. 87, No. 4, p. 261-271.
Salkie et al, Role of Clinical Laboratory in Allergy Testing, Clinical Biochemistry, 1994, vol. 27, No. 5, p. 343-355.
Bittner et al, Identification of wheat gliadins as an allergen family related to baker's asthma, Journal of Allergy and Clinical Immunology, 2007, vol. 121, No. 3, p. 744-749, Online Nov. 26, 2007.
Database UNIPROT, Accession No. P82977, Sequences last updated Jan. 9, 2007.
English translation of Office Action from corresponding JP 2010-535920, dated Dec. 17, 2013.
Bittner et al, "Identification and Characterization of an Allergen from Wheat," Conference Abstract from the 47th Congress of the German Society for Pneumology and Respiratory Medicine, Mar. 29-Apr. 1, 2006; Pneumologie Issue S 1, vol. 60, p. 259 (2006), and English Translation of Abstract.

* cited by examiner

Clone #10 Sequence:

```
1    ATG AGC CCT GTG GTG AAG AAG CCG GAG GGA GGG AAC ACC
     M   S   P   V   V   K   K   P   E   G   G   N   T    13
40   GAT ACT GGT GAC CAT CAC AAC CAG AAG ACG GAG TGG CCA
     D   T   G   D   H   H   N   Q   K   T   E   W   P    26
79   GAG TTG GTG GGG AAG TCG GTG GAG GAG GCC AAG AAG GTG
     E   L   V   G   K   S   V   E   E   A   K   K   V    39
118  ATT ATG CAG GAC AAG TCA GAG GCA CAG ATC GTA GTT CTA
     I   M   Q   D   K   S   E   A   Q   I   V   V   L    52
157  CCG GTG GGG ACA ATT GTG ACC ATG GAA TAT CGA ATC GAC
     P   V   G   T   I   V   T   M   E   Y   R   I   D    65
196  CGT GTC CGC CTC TTT GTT GAC AGT CTC GAC AAA ATT GCC
     R   V   R   L   F   V   D   S   L   D   K   I   A    78
235  CAG GTC CCC AGG GTC GGC tagcaagcttaagatctagcctgctcct
     Q   V   P   R   V   G                                 84
281  agcgtatatgtatcgtggcttgataatctcttcttggatatagcaagattga 333  gatatatagatcatatacaataagagttgatgcatggaaagtgaatggataa 385  tagaataagtcagagagcgcgtaaaaaaaaaaaa
```

Figure 1

WHEAT ALLERGENS

RELATED APPLICATIONS

The present application is a 371 of PCT/SE2008/051377 filed Nov. 28, 2008 and claims priority under 35 U.S.C. §119 to U.S. Application Ser. No. 60/991,338 filed Nov. 30, 2007.

FIELD OF THE INVENTION

The present invention relates to the field of IgE-mediated allergy, particularly occupational asthma such as baker's asthma. More specifically the invention relates to the identification of a novel wheat allergen and the use thereof in therapy and diagnosis. The invention also relates to methods for diagnosis and treatment of IgE-mediated allergy in mammals.

BACKGROUND

Allergens from wheat (*Triticum aestivum*) can cause three distinct IgE-mediated allergies, respiratory allergy by inhalation of wheat flour, food allergy by ingestion of wheat products and wheat pollen allergy which belongs to the group of grass pollen allergies. Allergic sensitization to wheat flour components is one of the most frequent causes of occupational asthma and approximately 1-10% of bakery workers are affected, therefore it is called baker's asthma. These bakery workers develop IgE antibodies against wheat flour allergens and flour-induced asthma and/or rhinitis. Support for the assumption that baker's asthma is a true occupational disease comes from the finding that the prevalence of sensitization to bakery-associated allergens is approximately tenfold higher in flour-exposed persons as compared to control populations without flour exposure. Furthermore, it has been possible to establish threshold values for wheat flour which are known to cause bronchial asthma in sensitized persons. A first systematic investigation on flour allergy was carried out already in 1933 by Baggoe. Other early reports focused on the description of cases of baker's asthma followed by mechanistic studies demonstrating the importance of IgE-mediated mechanisms in baker's asthma. Thereafter several attempts were made to characterize the disease-eliciting flour allergens by immunochemical methods, RAST technology, immunoblotting and recently by molecular cloning techniques.

*Triticum aestivum* is an important member of the grass family. Up to 40% of all allergic individuals carry serum IgE antibodies reacting with grass pollen allergens. Several studies have reported cross-reactivity between wheat flour and grass pollen due to common IgE epitopes in wheat flour and grass pollen proteins. Cross-reactivity between grass pollen allergens and wheat seed allergens has been described and there is evidence that patients suffering from bakers' asthma and IgE-mediated food allergy to wheat may recognize different allergens which may be used for the differential diagnosis of baker's asthma, food allergy flour to wheat and grass pollen allergy. However, the great majority of the soluble wheat flour allergens has not yet been identified. Today, only a few wheat flour allergens have been identified and characterized and they include the members of the alpha amylase inhibitor family, acyl-CoA oxidase, peroxidase, fructore-biphosphate aldolase and recently thioredoxins.

Diagnosis based on wheat flour extract does not discriminate between patients suffering from respiratory allergy or food allergy to wheat. Therefore precise diagnosis still relies on specific inhalation challenge in case of respiratory allergy to wheat flour and double-blind placebo-controlled food challenge (DBPCFC) in case of suspected food allergy and the question is open whether it is possible to identify allergens that can be used for selective diagnosis and treatment of the various wheat induced manifestations of allergy such as baker's asthma, food allergy and pollinosis. Thus there is a need to identify novel wheat allergens and to establish methods and diagnostic tests to specifically identify patients suffering from IgE-mediated allergy, such as respiratory allergy, e.g. baker's asthma, in order to discriminate them from patients suffering from food allergy and/or pollen allergy. Furthermore there is a need to use such novel wheat allergens for use in the treatment of IgE-mediated allergy. The present invention addresses these needs by providing novel wheat allergens and the use thereof in therapy and diagnosis. Furthermore the present invention provides the use of known peptides and proteins in therapy and diagnosis. Some of these peptides are known from Gennaro S. D. et al, Biological Chemistry, April 2005, 386:383-389; UNIPROT accession number P82977; UNIPROT accession number Q6W8Q2; U.S. Pat. No. 7,214,786 and US2006/0107345.

SUMMARY OF THE INVENTION

As stated above the few wheat flour allergens that have been identified and characterized include members of the alpha amylase inhibitor family, acyl-CoA oxidase, peroxidase, fructore-biphosphate aldolase and thioredoxins. So far no allergens have been identified that can be used for selective diagnosis and treatment of various wheat induced manifestations of allergy such as baker's asthma, food allergy and pollinosis. This led the present inventors to look for additional, not yet identified wheat allergens.

The present invention meets at least partly needs of prior art by providing novel wheat allergens and methods for diagnosis and treatment of IgE-mediated allergy in mammals.

In a first aspect the invention relates to polypeptides representing novel wheat allergens isolated from wheat or recombinantly produced and fragments or variants thereof sharing epitopes for antibodies. The isolated polypeptides comprise an amino acid sequence of clone #10, #112, or #126.

In a second aspect the invention relates to nucleic acids encoding the polypeptides of the invention, the nucleic acids having the nucleotide sequence of clone #10, #112, or #126.

In another aspect the invention relates to a polypeptide having clone identity #10, #38, #112, or #126 for use in therapy or diagnosis, preferably therapy and diagnosis of IgE-mediated allergy, such as respiratory allergy to wheat flour, e.g. baker's asthma. Furthermore the invention relates to an isolated polypeptide comprising the amino acid sequence of clone #37 for use in therapy or diagnosis, preferably therapy and diagnosis of IgE-mediated allergy, such as respiratory allergy to wheat flour, e.g. baker's asthma.

In still another aspect the invention provides a pharmaceutical composition comprising a polypeptide having clone identity #10, #38, #112, #126 or #37 or a hypoallergenic form thereof modified to abrogate or attenuate its IgE-binding response, and optionally pharmaceutically acceptable excipients, carriers, buffers and/or diluents. The hypoallergenic form of a polypeptide having clone identity #10, #38, #112, #126 or #37 may be modified by fragmentation, truncation or tandemerization of the molecule, deletion of internal segments, domain rearrangement, substitution of amino acid residues, disruption of disulfide bridges.

In a further aspect the invention relates to an allergen composition "spiked" with a polypeptide having clone identity #10, #38, #112, #126 or #37. Such an allergen composition may be an allergen extract or a mixture of purified or recombinant allergen components having no or a low content of the polypeptide of the invention, wherein the polypeptide is added in order to bind IgE from patients whose IgE would not bind or bind poorly to the other allergen components in the composition. This aspect of the invention also relates to a method for producing such a composition, which method comprises the step of adding a polypeptide having clone identity #10, #38, #112, #126 or #37 to an allergen composition, such as an allergen extract (optionally spiked with other components) or a mixture of purified native or recombinant allergen components.

In a further aspect the invention relates to an allergen composition obtainable by the above method.

The invention further relates to a method for in vitro diagnosis of IgE-mediated allergy comprising the steps of bringing a body fluid sample, such as a blood, plasma or serum sample, from a mammal suspected of having IgE-mediated allergy such as respiratory allergy to wheat flour, e.g. baker's asthma, in contact with the polypeptide having clone identity #10, #38, #112, #126 or #37, and detecting the presence, in the sample, of IgE antibodies that bind specifically to the polypeptides of the invention. The presence of such antibodies specifically binding to the polypeptide having clone identity #10, #38, #112, #126 or #37 is indicative of IgE-mediated allergy. One embodiment of such a method comprises carrying out the method by micro-array analysis.

In a further aspect the invention provides a diagnostic kit for performing the method of in vitro diagnosis of IgE-mediated allergy, such as respiratory allergy to wheat flour, e.g. baker's asthma, said kit comprising a polypeptide having clone identity #10, #38, #112, #126 or #37, and means for detecting the IgE binding to said polypeptide, such as a solid support, e.g. a nitrocellulose membrane or a microarray having a polypeptide with clone identity #10, #38, #112, #126 or #37 bound thereto.

In still a further aspect the invention provides a method for treatment of an IgE-mediated allergy in a mammal, such as respiratory allergy, e.g. baker's asthma. In one embodiment the method comprises administering to an individual susceptible to such a treatment a polypeptide having clone identity #10, #38, #112, #126 or #37 or a fragment or a variant thereof sharing epitopes for antibodies. In another embodiment the method comprises administering to an individual susceptible to such a treatment a pharmaceutical composition according to a previous aspect.

DEFINITIONS

TABLE A

Definition of clones

| Clone | Nucleic acid sequence | Amino acid sequence |
| --- | --- | --- |
| #10 | SEQ ID NO: 1 | SEQ ID NO: 2 |
| #37 | SEQ ID NO: 3 | SEQ ID NO: 4 |
| #38 | SEQ ID NO: 5 | SEQ ID NO: 6 |
| #112 | SEQ ID NO: 7 | SEQ ID NO: 8 |
| #126 | SEQ ID NO: 9 | SEQ ID NO: 10 |

Variants and fragments of a polypeptide of the invention should be construed as meaning proteins or peptides with a length of at least 10 amino acids, more preferably at least 25, even more preferably at least 50 or 75 amino acid residues and a sequence identity to said polypeptide of at least 50%, preferably over 60%, 70%, 80%, 90%, 95%, 96%, 97%, 98% or 99%.

A modified polypeptide should in the context of the present invention be construed as meaning a polypeptide that has been chemically or genetically modified to change its immunological properties, e.g. as exemplified in relation to the immunotherapy aspect of the invention.

Variants and fragments of a polypeptide sharing epitopes for antibodies with said polypeptide should be construed as being those fragments and variants whose binding of IgE antibodies from a serum sample from a representative patient sensitized with the polypeptide of the invention can be significantly inhibited by the polypeptide. Such an inhibition assay may e.g. be performed according to the protocol disclosed in Example 4.

A hypoallergenic modified polypeptide or variant or fragment of a polypeptide should be construed as being a modified polypeptide or variant or fragment of a polypeptide that is not capable of binding IgE antibodies reactive to said polypeptide from a serum sample of a representative polypeptide-sensitized patient, as determined e.g. by the protocol according to Example 1 or which displays no or significantly reduced biological allergen activity, as determined by a cellular activation assay such as the basophil histamine release assay.

BRIEF DESCRIPTION OF TABLES AND FIGURES

Table I shows the demographic, clinical and serological characteristics of patients suffering from bakers' asthma.

Table II shows the demographic, clinical and serological characteristics of patients suffering from food allergy to wheat (F1-F4) and grass pollen allergy (G1-G4).

Table III shows the percentage amino acid sequence identities between the clone 10-derived allergen and homologous proteins, wherein proteins numbered 1-30 are the following: 1. gi|122065237 (*Triticum aestivum*), 2. gi|66356278 (*Triticum aestivum*), 3. gi|124122 (*Hordeum vulgare* subsp. *vulgare*), 4. gi|48093360 (*Zea diploperennis*), 5. gi|48093418 (*Tripsacum dactyloides*), 6. gi|75994161 (*Zea mays* subsp. *parviglumis*), 7. gi|58396945 (*Oryza sativa* [japonica cultivar-group]), 8. gi|115649132 (*Strongylocentrotus purpuratus*), 9. gi|37904392 (*Brachypodium distachyon*), 10. gi|26224744 (*Citrus×paradise*), 11. gi|224447 (*Vicia faba*), 12. gi|124395862 (*Paramecium tetraurelia*), 13. gi|50262213 (*Cucurbita maxima*), 14. gi|547743 (*Nicotiana sylvestris*), 15. gi|54610713 (*Lumbricus terrestris*), 16. gi|169491 (*Solanum tuberosum*), 17. gi|218290 (*Nicotiana glauca×Nicotiana langsdorffii*), 18. gi|124121 (*Vigna angularis*), 19. gi|603890 (*Sambucus nigra*), 20. gi|14718445 (*Ipomoea batatas*), 21. gi|114950 (*Momordica charantia*), 22. gi|109138554 (*Fagopyrism esculentum*), 23. gi|18404883 (*Arabidopsis thaliana*), 24. gi|27734408 (*Canavalia lineate*), 25. gi|37901103 (*Hevea brasiliensis*), 26. gi|92874842 (*Medicago truncatula*), 27. gi|13959383 (*Linum usitatissimum*), 28. gi|22759723 (*Zinnia elegans*), 29. gi|37359345 (*Vitis vinifera*) and 30. gi|6453287 (*Amaranthus hypochondriacus*).

Table IV shows clinical data for baker's asthma patients of Example 2.

Table V shows clinical data for food and grass pollen allergic patients of Example 2.

Table VI shows PCR primers used for amplification of cDNAs for clones #10, #38, #112, #123 #126 and #37.

Table VII. Demographic, clinical and serological characteristics of patients suffering from baker's asthma Table VIII. Demographic, clinical and serological characteristics of patients suffering from grass pollen allergy Table IX. Demographic, clinical and serological characteristics of patients suffering from food allergy to wheat FIG. 1 illustrates the nucleotide and deduced amino acid sequence of the clone 10-derived allergen (SEQ ID NO: 1). Coding and non-coding region are in upper and lower case letters, respectively, the start (ATG) and stop codons are underlined. Amino acids of the potato inhibitor I family signature are printed with grey background. Left hand numbers are for the nucleotides and right hand numbers for the amino acids. The sequence has been submitted to the GenBank under the accession number (EU051824).

FIG. 2 illustrates the characterization of purified serine proteinase inhibitor-like allergen. A, Coomassie brilliant blue-stained SDS-PAGE containing purified clone 10-derived allergen. A molecular weight marker (kDa) is shown on the left side. B, Mass spectrometry (MS) of the purified clone 10-derived allergen. The mass/charge ratio is shown on the x-axis and the intensity is displayed on the y-axis as a percentage of the most intensive signal obtained in the investigated mass range. C, Far-ultraviolet circular dichroism (CD) analysis of the purified clone 10-derived allergen. The spectra are expressed as mean residue ellipticities ($\theta$) (y-axis), recorded at 25° C. (bold line), 95° C. (regular line) and 25° C. after cooling (dotted line) at given wave lengths (x-axis).

Figure 3:
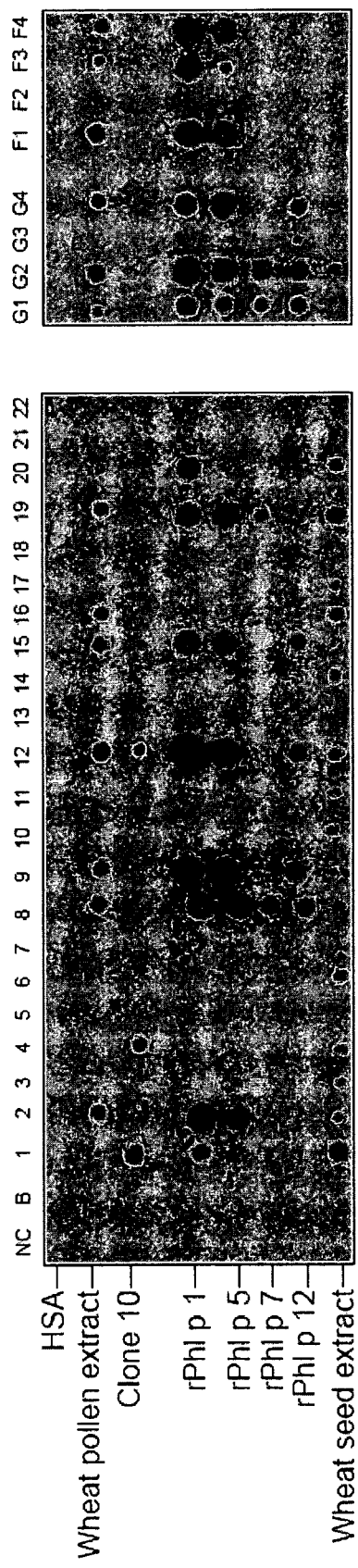

FIG. 3 illustrates the IgE reactivity of patients suffering from bakers' asthma, grass pollen allergy and food allergy. Purified clone 10-derived allergen, HSA, rPhl p 1, rPhl p 5, rPhl p 7, rPhl p 12, wheat pollen extract and wheat seed extract were dotted onto nitrocellulose membrane strips and incubated with sera from 22 bakers' asthma patients (1-22), four grass pollen allergic patients sera (G1-04), four sera from patients suffering from food allergy to wheat (F1-F4), one non-allergic individual (NC) and buffer without addition of serum (B). Bound IgE antibodies were detected with $^{125}$I-labelled anti-human IgE antibodies and visualized by autoradiography.

Figure 4:
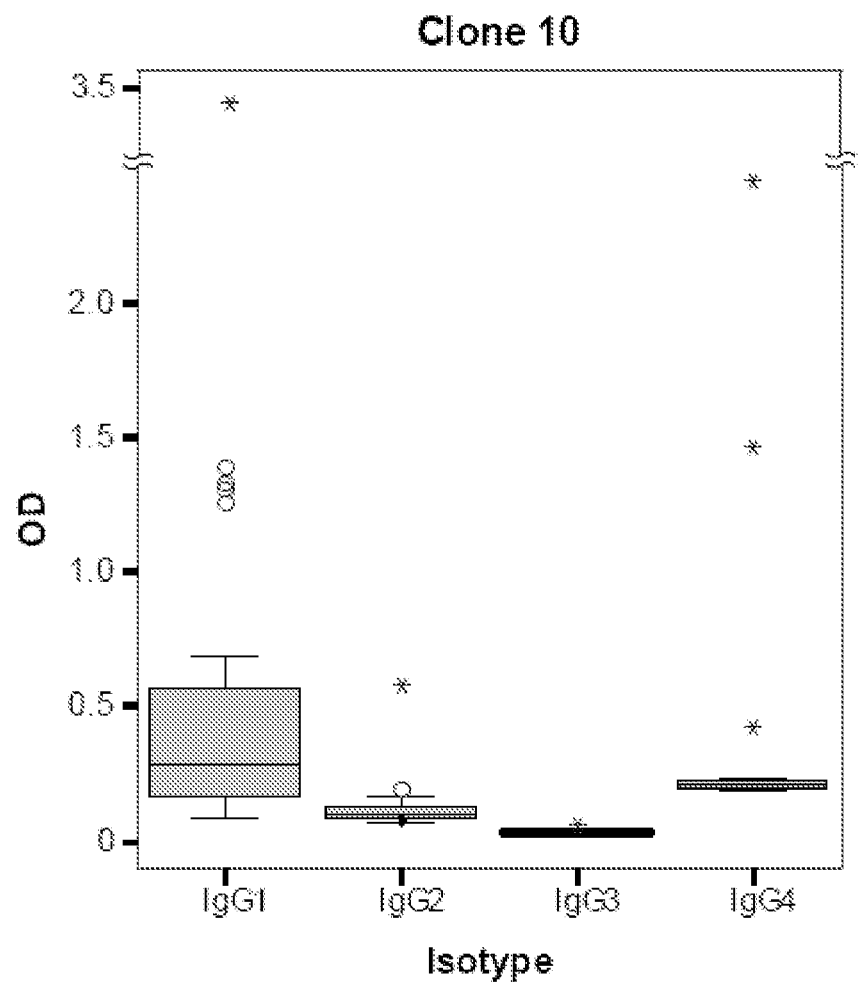

FIG. 4 is a box plot representation of IgG subclass reactivities to clone 10-derived allergen. IgG$_{1-4}$ subclass reactivities to the clone 10-derived allergen were determined by ELISA for patients suffering from bakers' asthma (n=22) and are displayed as box plots where 50% of the values are within the boxes and non-outliers between the bars. The lines within the boxes indicates the median values, circles are outliers and asterisks extreme values.

Figure 5:
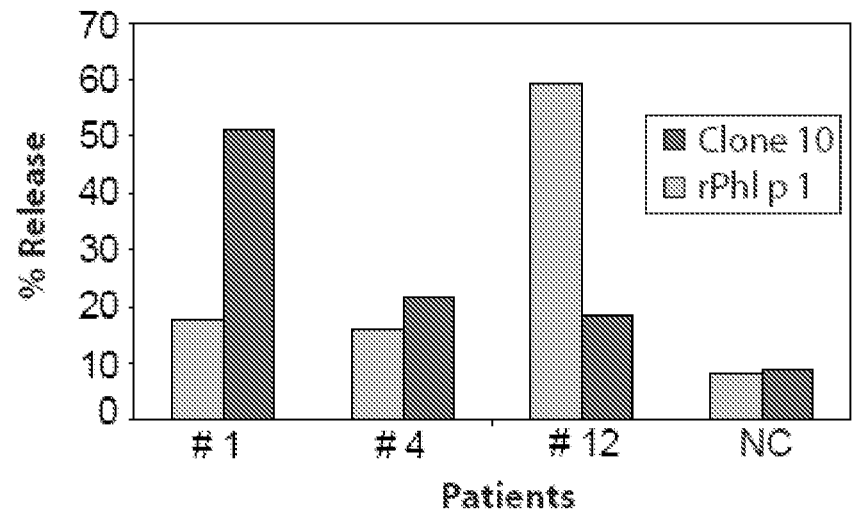

FIG. 5 illustrates the allergenic activity of the clone 10-derived allergen. RBL cells were loaded with serum IgE from three bakers' asthma patients (#2, #4, #12) or with serum of a non-allergic patient (NC) and then challenged with recombinant clone 10-derived allergen or timothy grass pollen allergen rPhl p 1. The mean β-hexosaminidase releases are shown on the y-axis as percentages of total release after subtraction of percentages for spontaneous release.

Figure 6:
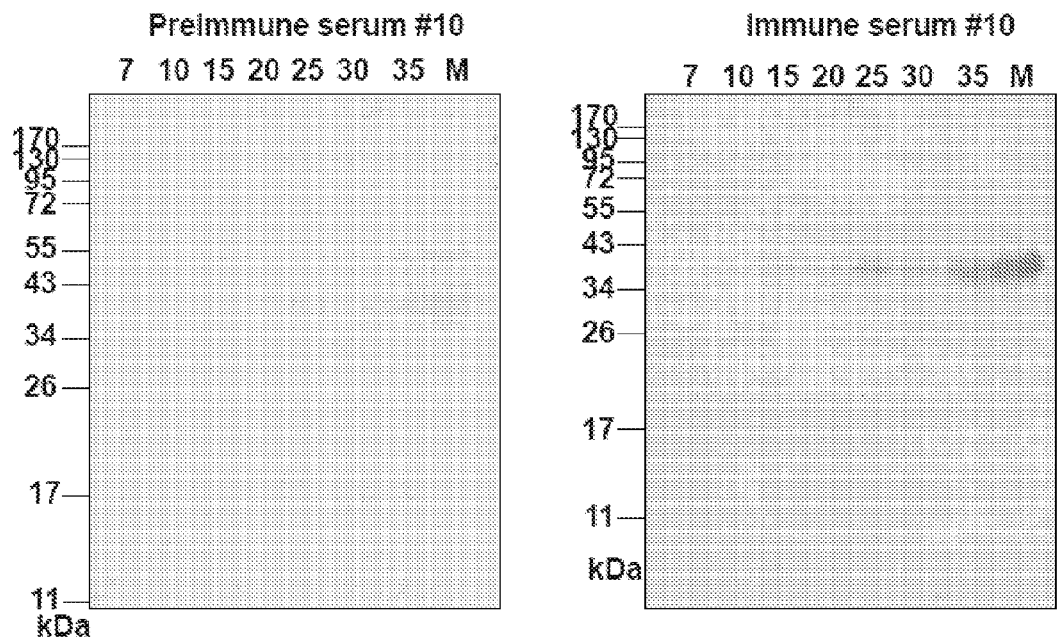

FIG. 6 shows the expression of the serine proteinase inhibitor-like allergen in seeds during seed maturation. Nitrocellulose-blotted wheat extract from immature (day 7, 10, 15, 20, 25, 30, 35) and mature (M) wheat seeds were probed with rabbit antibodies specific for the clone 10-derived allergen, and for control purposes, with the corresponding pre-immune serum. Molecular weights are indicated on the left side in kilo Dalton (kDa).

Figure 7:
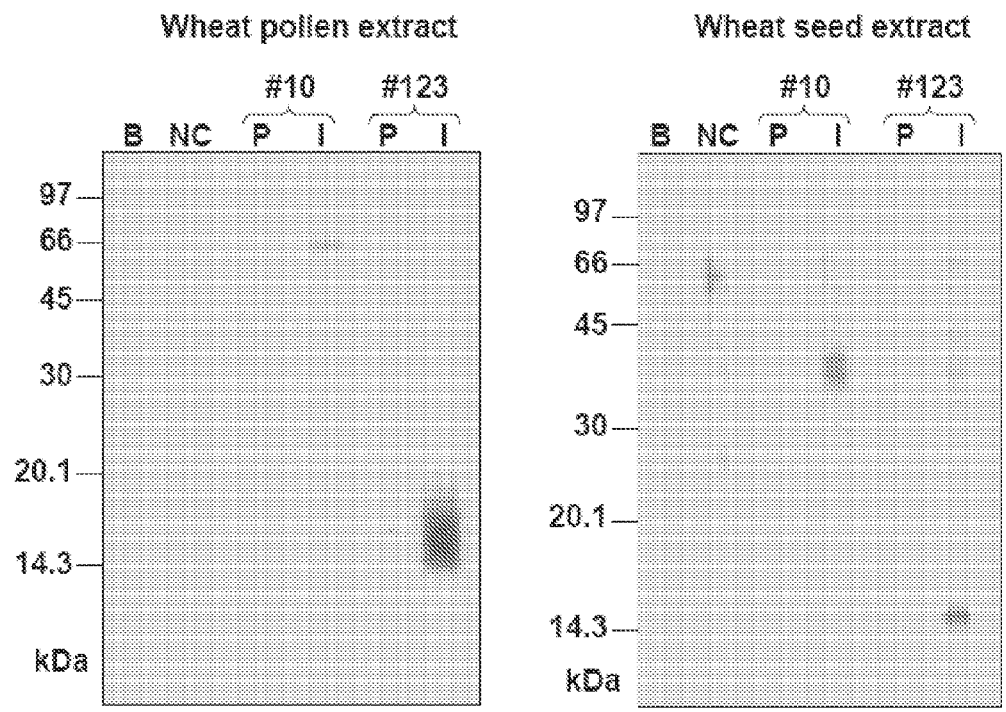

FIG. 7 shows the identification of the clone 10-derived allergen in wheat pollen and seed extracts. Nitrocellulose blotted extracts were probed with rabbit antibodies specific for the clone 10-derived allergen (20), antibodies specific for wheat profilin (I #123), for a mite allergen (NC) or with buffer without addition of rabbit antibodies (B). The corresponding pre-immune sera are referred as P #10 and P #123 respectively. Bound IgG antibodies were detected with $^{125}$I-labelled donkey anti-rabbit antibodies and visualized by autoradiography. Molecular weight markers (in kDa) are indicated on the left.

Figure 8:
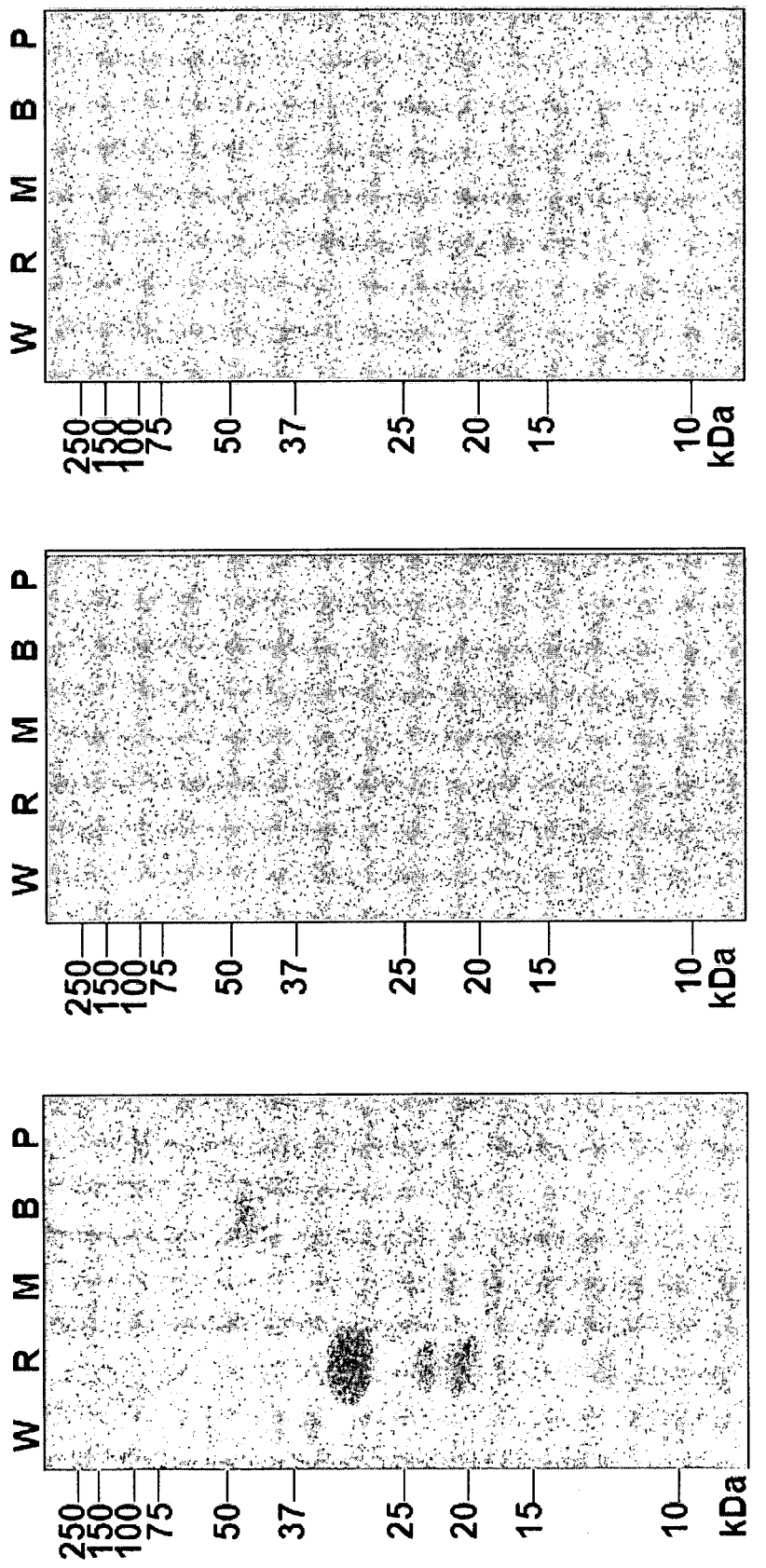

FIG. 8 illustrates the detection of the serine proteinase inhibitor-like allergen in extracts from wheat seeds, rice, maize, bean and potato. A, Coomassie blue-stained gel containing extracts from wheat (W), rice (R) and maize (M), common bean (B) and potato (P). B, Nitrocellulose blotted extracts were exposed to rabbit pre-immune serum and C, rabbit antibodies specific for the clone 10-derived allergen. Molecular masses (kDa) are indicated on the left side.

Figure 9:
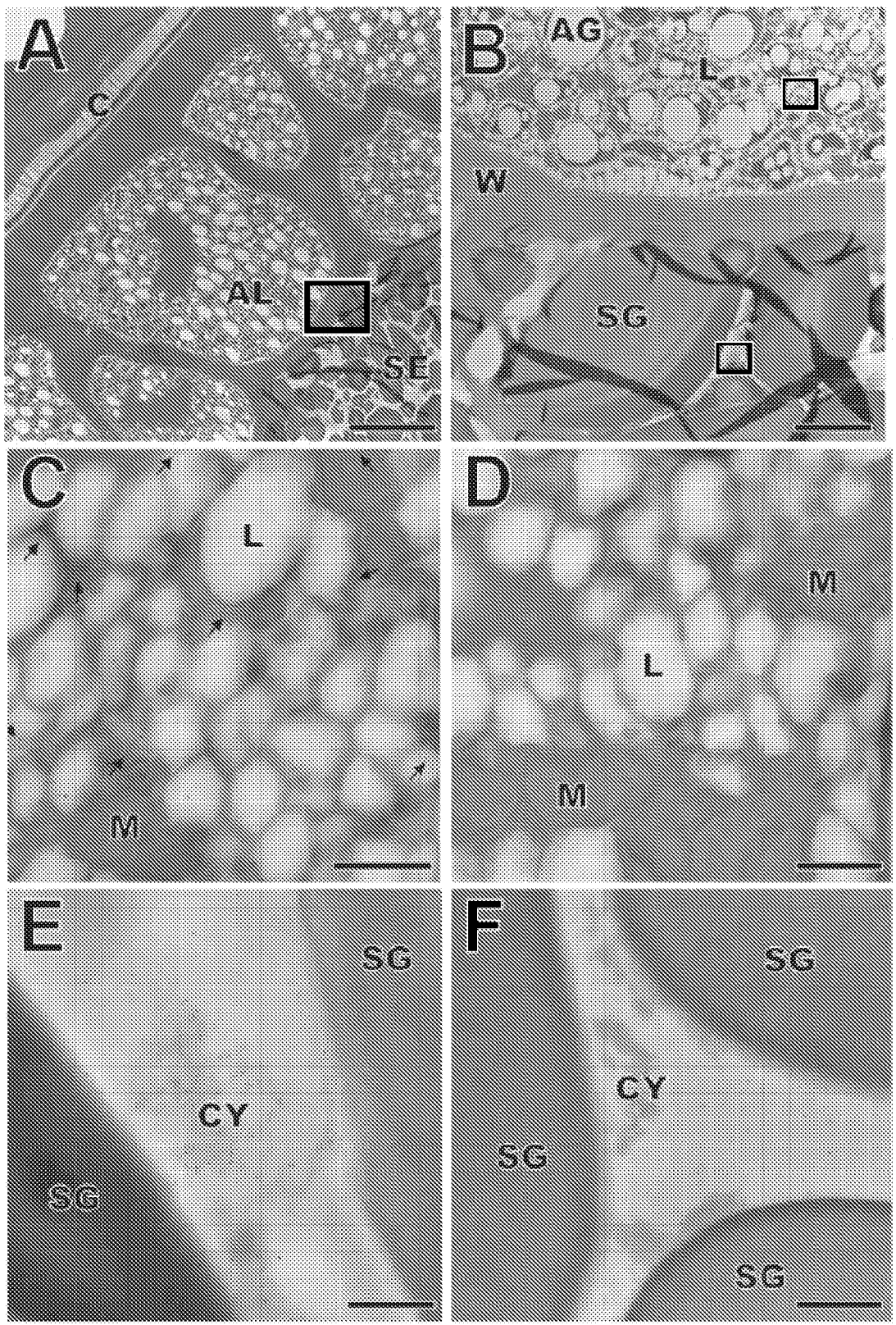

FIG. 9 shows the localization of clone 10-derived allergen by transmission immunogold electron microscopy in a wheat seed. A and B, Cross section of a wheat grain at low (A) and high (B) magnification. A shows fruit and seed coat (C), aleuron layer (AL) and the beginning of the starchy endosperm (SE). The rectangle in A indicates an area comparable to the area shown in B, i.e. border between aleuron layer and starchy endosperm. The rectangles in B indicate areas shown in high magnification in C, D and E, F, respectively. C and D, Detail of a wheat seed aleurone cell probed with rabbit anti-clone 10 derived Ig (C) or preimmune Ig (D). E and F, High magnification micrograph of the starchy endosperm after immunogold localization of wheat protein 10 with rabbit anti-clone 10 derived Ig (E) or preimmune Ig (F). Bound rabbit antibodies were detected with a gold-conjugated goat anti-rabbit Ig antiserum (gold particles=black dots). Arrows point to colloidal gold particles. The bars represent: A, 20 μm; B, 5 μm; C—F, 0.5 μm. AG, aleuron grain; AL, aleuron layer; C, multilayered fruit and seed coat; CY, cytoplasmic materials; L, lipid body; M, mitochondrion; SE, starchy endosperm; SG, starch grain; W, cell wall.

Figure 10:
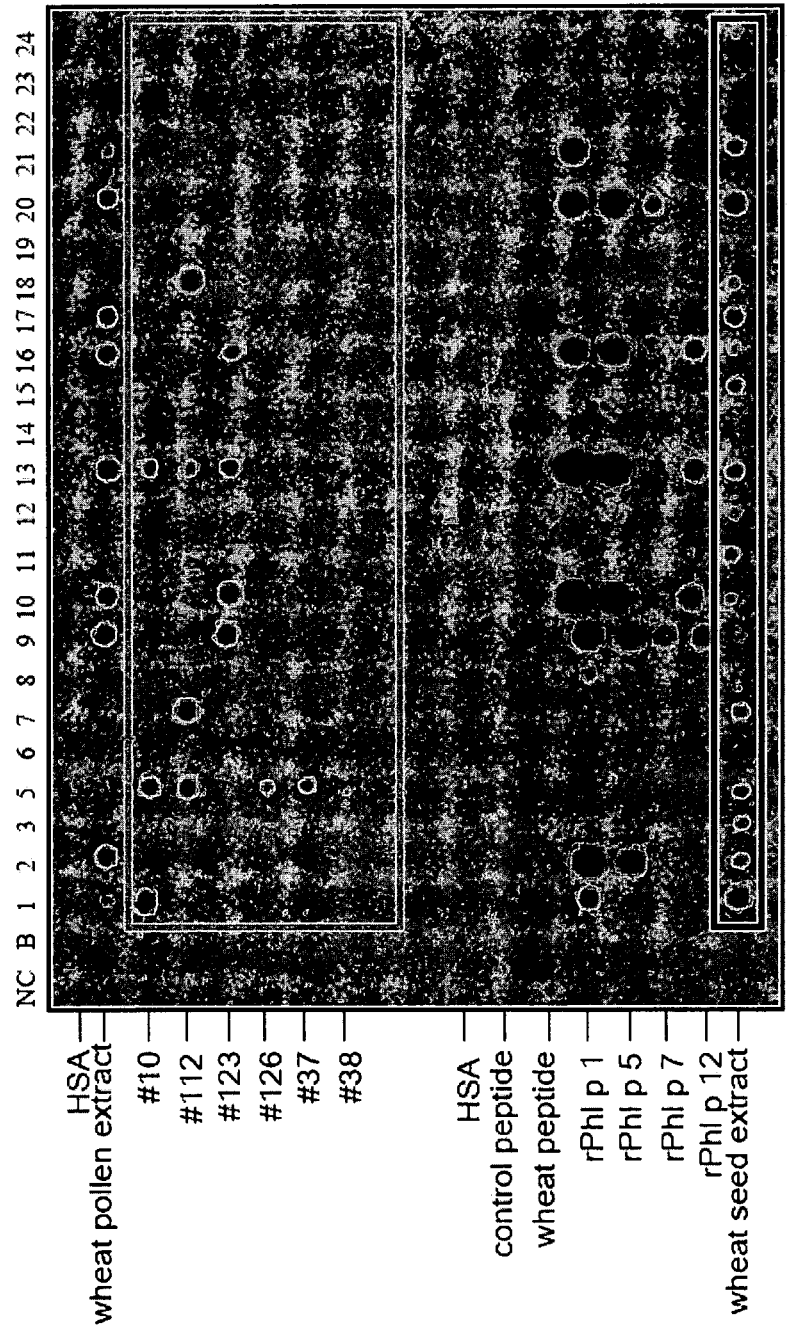

FIG. 10. IgE Dot Blot of patients suffering from baker's asthma.

Figure 11:
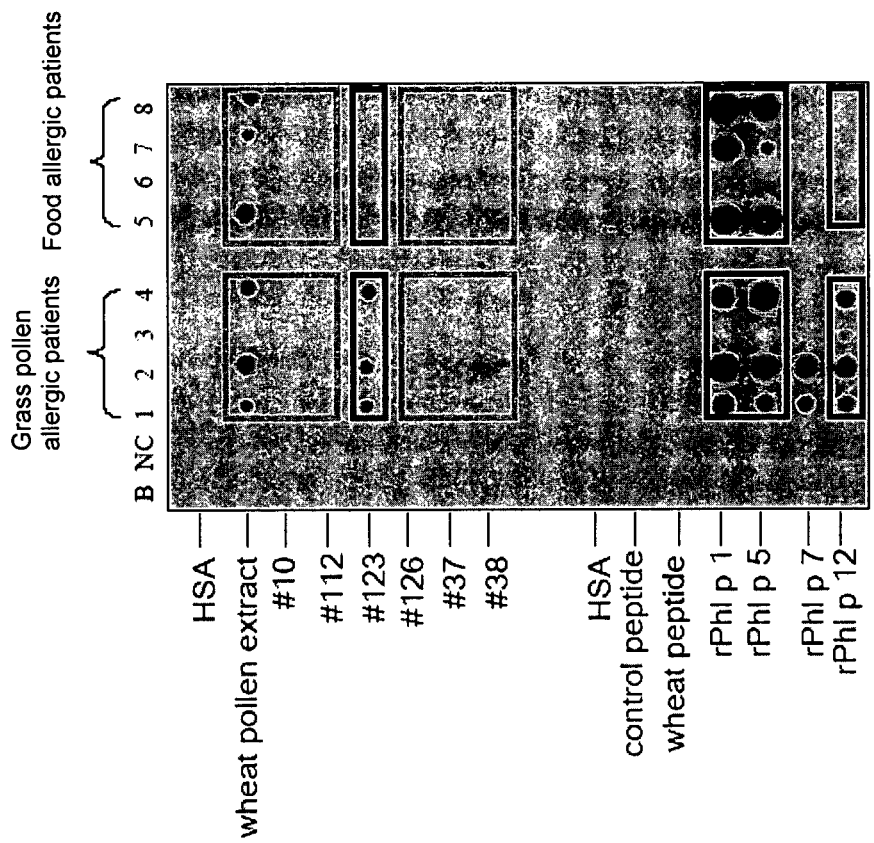

FIG. 11. IgE Dot Blot of patients suffering from food allergy to wheat and grass pollen allergy.

Figure 12:
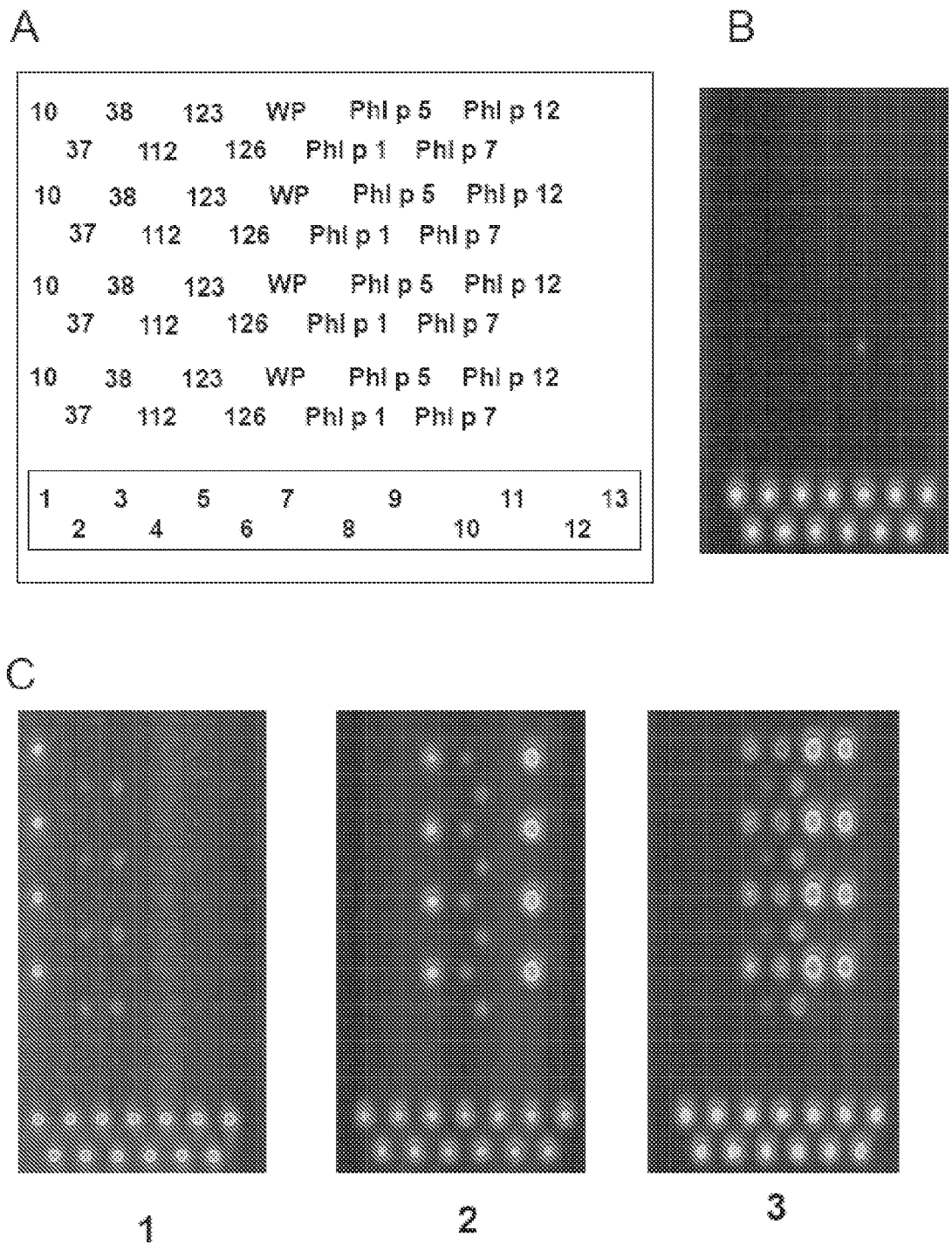

FIG. 12. Allergen microarray. A, Application scheme of micro-arrayed proteins and wheat pollen extract. Recombinant wheat proteins are designated as: 10, 37, 38, 112, 123, 126; WP: wheat pollen extract; recombinant timothy grass pollen allergens: Phl p 1, Phl p 5, Phl p 7 and Phl p 12. Numbers in the box at the bottom indicate position markers. B and C, Images of microarrays after incubation with serum and detection of IgE-reactive spots with fluorophore-conjugated anti-IgE antibodies. B, Image after incubation with serum from a non allergic individual. C, Images after incubation with serum from a representative patient suffering from baker's asthma (1: B4), wheat induced food allergy (2: F26), grass pollen allergy (3: G16). Dots on the bottom of the slides indicate position markers which are purified IgE antibodies detected with fluorophore-conjugated anti-IgE antibodies.

Figure 13A:
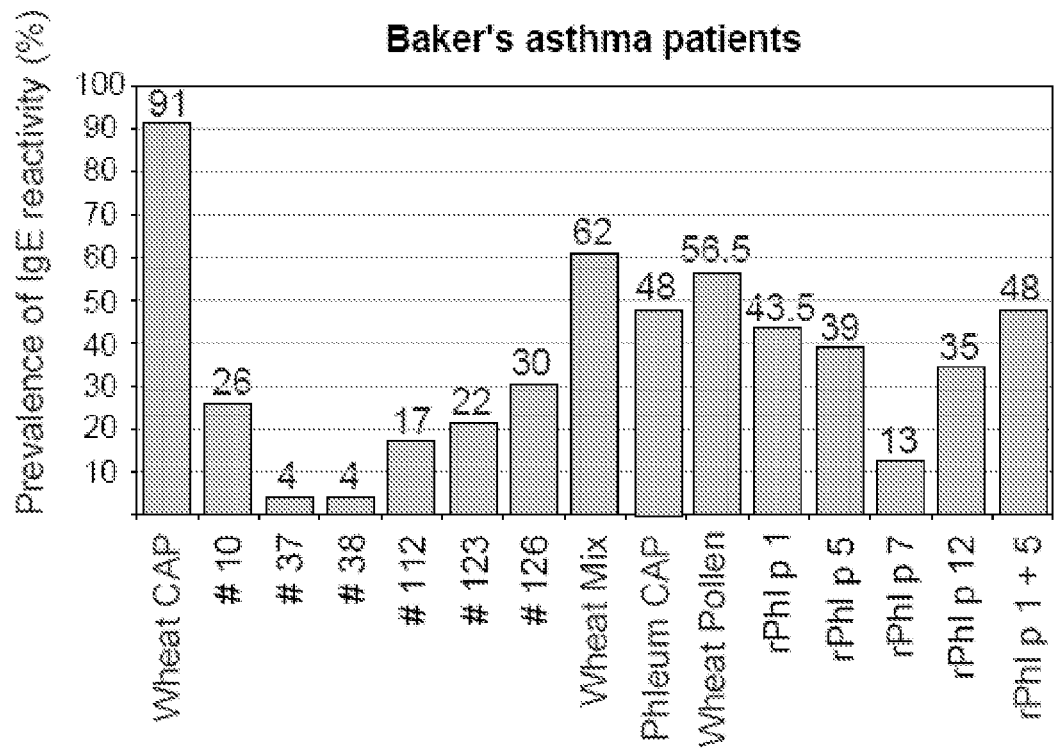
Figure 13B:
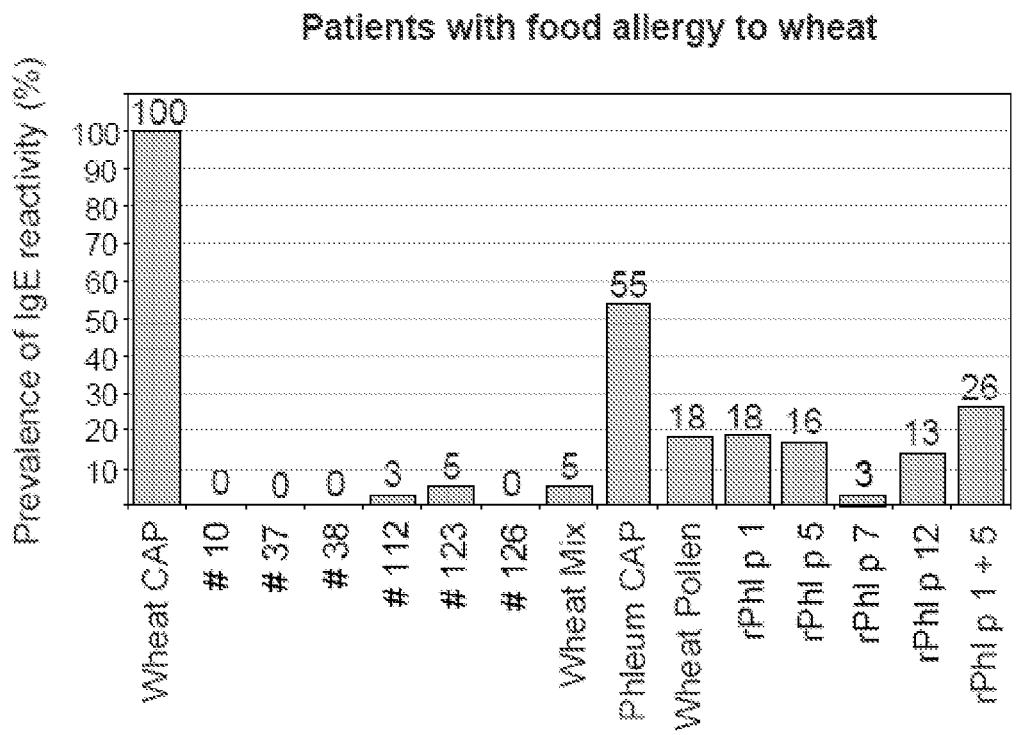
Figure 13C:
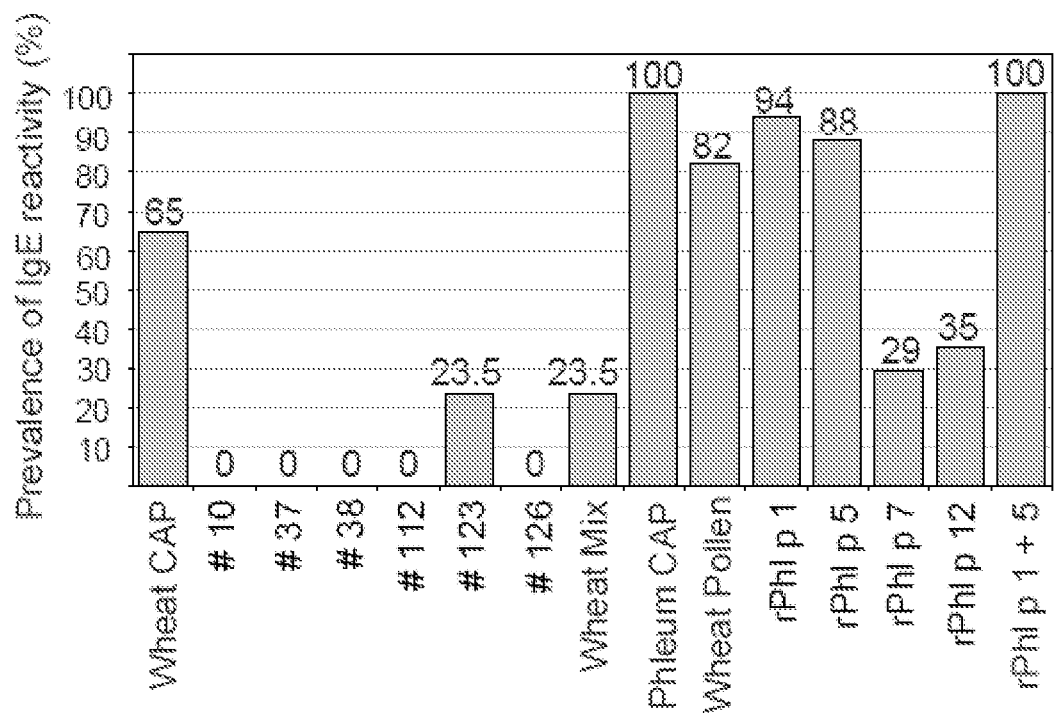

FIG. 13. Prevalence of IgE reactivity to wheat seed proteins, wheat pollen extract and grass pollen allergens. Percentages of patients with IgE reactivity are shown for baker's asthma (A) (n=23), food allergy to wheat (B) (n=38) and grass pollen allergy (C) (n=17) at the y-axis. The x-axis shows the tested recombinant wheat proteins #10, #37, #38, #112, #123 and #126, wheat pollen extract, recombinant grass pollen allergens Phl p 1, Phl p 5, Phl p 7 and Phl p 12, a "Wheat Mix" comprising all recombinant wheat proteins, wheat flour and timothy grass CAP used to measure IgE reactivity.

DETAILED DESCRIPTION OF THE INVENTION

The examples below illustrate the present invention with the isolation and use of the polypeptide of the invention. The examples are only illustrative and should not be considered as limiting the invention, which is defined by the scope of the appended claims. Clone #123 mentioned in the Examples is profilin, known from e.g. U.S. Pat. No. 7,214,786.

EXAMPLE 1

The Novel Wheat Allergen Clone #10

Example 1 shows the identification and characterization of a novel wheat seed allergen, clone #10, belonging to the potato inhibitor family, a family of serine protease inhibitors, which together with other protease inhibitors are referred to as pathogenesis related proteins (PR), family PR6. Clone #10 is the first allergen identified and described for the PR6 family. Furthermore Example 1 shows the expression and purification of a recombinant clone 10-derived allergen.

Clone #10 was specifically recognized by serum IgE from patients with baker's asthma but showed no IgE reactivity when tested with sera from patients suffering from food allergy to wheat, celiac disease or grass pollen allergy. Therefore the clone 10-derived allergen together with other wheat allergens may be used to establish diagnostic tests which allow to specifically identify patients suffering from IgE-mediated baker's asthma and to discriminate these patients from allergic patients with food or pollen allergy.

Techniques

Biological Materials, Patients' Sera and Antibodies

Wheat seeds from *Triticum aestivum* cv. Michael were obtained from the Österreichische Agentur für Gesundheit and Ernährungssicherheit GmbH and planted in a glasshouse. Immature seeds were harvested 7, 10, 15, 20, 25, 30 and 35 days after the onset of pollination directly into liquid nitrogen and stored at −80° C. until use. Wheat pollen was obtained from Allergon (Välinge, Sweden). Rice, maize, beans and potatoes were bought at a local market. Recombinant Phl p 1, Phl p 5, Phl p 7 and Phl p 12 were purchased from BIOMAY (Vienna, Austria) and human serum albumin (HSA) from Behring (Marburg, Germany). Sera were obtained from 22 patients suffering from bakers' asthma. Baker's asthma was diagnosed on the basis of a positive case history, IgE specific for wheat and rye flour by CAP-FEIA System (Phadia, Uppsala, Sweden) and included specific inhalation challenge tests for confirmation of a clinically relevant sensitization (1). Demographic, clinical and serological data of these patients are summarized in Table I. In addition, serum from a non-allergic individual, sera from 4 patients suffering from food allergy to wheat and 4 grass pollen allergic patients without baker's asthma but serum IgE reactivity to wheat and rye flour were included in the experiments (Table II). Sera from grass pollen allergic patients had been analyzed for total serum IgE levels and IgE specific timothy grass pollen by CAP-FEIA System (Phadia) and patients with food allergy to wheat have been characterized as described previously (2). The specificity of the clone 10-derived allergen for baker's asthma was confirmed by testing additional 20 sera from celiac disease patients, 119 food allergic patients, 23 sera from grass pollen allergic patients and 25 baker's asthma patients by chip analysis (Constantin et al, unpublished).

Specific rabbit antibodies against the clone 10-derived allergen were raised by immunization of a rabbit in monthly intervals with purified clone 10-derived allergen (200 μg per injection) using once Freud's complete adjuvant and twice IFA (Charles River, Kisslegg, Germany). Pre-immune serum was obtained from the rabbit before immunization. For control purposes, a rabbit immune serum specific for a house dust mite allergen and rabbit antiserum specific for wheat profilin were used.

Construction of a λgt11 cDNA Library from Wheat Seeds

Total RNA was extracted according to Yeh (3) from wheat seeds, harvested twenty five days after the onset of pollination, and stored at −80° C. Then the RNA pellet was dissolved in guanidinium isothiocyanate buffer (4M guanidinium isothiocyanate, 0.83% v/v 3M sodium acetate, pH 6, 11 mM β-mercaptoethanol) and purified by cesium chloride density gradient ultracentrifugation (4). Poly-A$^+$ RNA was isolated by oligo-dT cellulose affinity chromatography (Nucleo Trap mRNA; Machery-Nagel) and double stranded cDNA was synthesized with a cDNA synthesis kit (cDNA synthesis System; Roche Diagnostics, Mannheim, Germany). After methylation with EcoRI methylase (New England Biolabs, Beverly, Mass.), EcoRI linkers (New England Biolabs) were added to the cDNA. Linkered cDNA was digested with EcoRI (Roche Diagnostics). Digested linkers were removed with a Nick column (Pharmacia Biotech, Uppsala, Sweden) and the cDNA was ligated into λgt11 arms (Stratagene, La Jolla, Calif., USA). The ligation product was packed in vitro (Gigapack III Gold Cloning Kit, Stratagene) resulting in a λgt11 expression cDNA library with 2.43×10$^6$ PFU.

Isolation and Characterization of IgE-Reactive Clones from a Wheat Seed cDNA Library

*E. coli* Y1090 were infected with 7×10$^5$ PFU of recombinant phages and immunoscreened with serum IgE of four patients (#1, #2, #4, #12) suffering from bakers' asthma as described (5). Fifteen IgE-reactive phage clones were selected for further re-cloning and their DNA was PCR-amplified using Platinum PCR Supermix (Invitrogen, Life Technologies) with λgt11 primers and sequenced (MWG, Ebersberg, Germany). The obtained sequences were compared with sequences submitted to the GenBank database at the National Center for Biotechnology Information (NCBI). Multiple sequence alignment was performed using the GenBank database at the NCBI. For amino acid sequence identities the Clustal W multiple alignment tool was used. A motif search was carried out with the PROSITE tool of the ExPASy proteomics server, for amino acid composition the ProtParam tool of ExPASy was used. Solvent accessibility and secondary structure prediction was calculated using the PROT software from the Columbia University Bioinformatics Center. A phylogenetic tree was reconstructed based on the amino acid sequence of the clone 10-derived allergen and homologous proteins using the "Multiple Alignment and Phylogenetic Tree Reconstruction" software provided by the Max Planck Institute for Molecular Genetics.

Expression and Purification of the Clone 10-Derived Recombinant Allergen

The coding region of the clone 10 cDNA was amplified by PCR using the following primer pair: forward 5'-CATAT-GAGCCCTGTGGTGAAGAAGCCGGAGGGA-3' and reverse, 5'-GAATTCTTAGTGATGGTG-ATGGTGATGGCCGACCCTGGGGAC-3' (MWG). The PCR product contained NdeI (italics), EcoRI (underlined) restriction sites and a hexahistidine tag-encoding sequence (bold). The PCR product was subcloned into an AccepTor Vector (Novagen, Madison, Wis.) and sequenced again (MWG). Then the insert was cut out of the AccepTor Vector with NdeI and EcoRI (Roche Diagnostics), gel-purified (Promega, Madison, Wis., USA) and subcloned into the expression plasmid pET 17b (Novagen). The DNA sequence was confirmed by sequencing both DNA strands (Microsynth, Balgach, CH). The pET 17b-clone 10 construct was transformed into *E. coli* BL21 (DE3) (Stratagene) and grown in Luria Broth (17) medium containing 100 mg/l ampicillin at 37° C. to an OD (600 nm) of 0.8-1. Protein expression was induced by addition of isopropyl β-D-thiogalactopyranoside (IPTG) to a final concentration of 0.5 mM and growing the bacteria for additional 3 h. Bacteria were harvested by centrifugation and—homogenized in 25 mM imidazole, pH 7.5, 0.1% (v/v) Triton X-100 with an Ultraturrax (IKA, Stauffen, Germany). DNA was digested by addition of DNase I, stirred for additional 10 min at 20° C., the reaction was stopped with 200 µl of 5M NaCl and then centrifuged at 4° C. (6000×g, 20 min). The majority of the clone 10-derived allergen was found in the insoluble fraction of the bacterial extract. Clone 10-derived allergen was purified from the inclusion body-containing pellet under denaturing conditions using Ni-NTA resin affinity columns according to the QIAexpressionist handbook (QIAGEN, Hilden, Germany). Fractions containing the recombinant allergen were pooled and dialyzed against 10 mM $NaH_2PO_4$ pH 7.5. The protein concentration was determined with a Micro BCA Protein Assay Kit (Pierce, Rockford, Ill.).

ELISA

Clone 10-derived allergen was dissolved in PBS at a concentration of 5 µg/ml and coated on ELISA plates (Nunc Maxisorb, Roskilde, Denkmark). After blocking with 1% (w/v) BSA in PBS, 0.05% (v/v) Tween 20 (PBST), plates were incubated with sera diluted 1:50 in PBST, 0.5% (w/v) BSA for measurement of $IgG_1$, $IgG_2$, $IgG_3$ and $IgG_4$ as described (6). Bound antibodies were detected by incubating first with monoclonal mouse anti-human IgG subclass antibodies (BD Biosciences, Franklin Lakes, N.J.) diluted 1:1000 in PBST, 0.5% (w/v) BSA, and then with a horseradish-peroxidase-coupled sheep anti-mouse antiserum (GE Healthcare, Little Chalfont, UK) diluted 1:2000 in PBST, 0.5% (w/v) BSA as previously described (2). All determinations were performed as duplicates, and results are expressed as mean values.

Protein Extracts, SDS-PAGE and Immunoblots

SDS-protein extracts from mature and immature wheat seeds, rice (*Oryza sativa*), maize (*Zea mays*), common bean (*Phaseolus vulgaris*) and potato (*Solanum tuberosum*) were prepared by homogenization of 3 grams of tissue in 32 ml of sample buffer (6) and subsequent boiling for 10 minutes. In order to remove insoluble particles, the extracts were centrifuged at 10,000×g for 10 min at 4° C. and the supernatants were stored in aliquots at −20° C. In addition a PBS-protein extract from wheat seeds was prepared as previously described (2). *Triticum aestivum* pollen (500 mg) were extracted at 4° C. over night in 5 ml PBS, 2 mM EDTA, 1 mM PMSF. After centrifugation for 1 h at 13,000×g 4° C., the protein concentration of the supernatant was determined with Micro BCA Protein Assay Kit (Pierce) and aliquots were stored at −20° C. until use. Equal amounts of SDS-protein extracts were separated by 14% preparative SDS-polyacrylamide gels (7). A protein molecular weight marker (Rainbow Marker, GE Healthcare; Precision Plus Protein Standard, BioRad, Herkules, Calif.; Page Ruler Pre-stained Protein Ladder, Fermentas, Burlington, Ontario) was used as a standard. After electrophoretic separation, proteins were either stained with Coomassie brilliant blue or blotted onto nitrocellulose membranes (Schleich 85 Schuell, Dassel, Germany) (8). Membranes were blocked in buffer A (50 mM sodium phosphate buffer, pH 7.4, 0.5% w/v BSA, 0.5% v/v Tween-20, 0.05% w/v $NaN_3$) twice for 10 min and once for 30 min and incubated overnight at 4° C. with a rabbit antiserum specific for the clone 10-derived allergen, the corresponding pre-immune serum, and for control purposes, with a rabbit antiserum specific for an unrelated antigen or buffer alone. Rabbit sera were diluted 1:50,000 in buffer A. Bound antibodies were detected with 1:2000 in buffer A diluted $^{125}I$-labelled anti-rabbit antibodies from donkey (GE Healthcare) for 2 h at room temperature and visualized to Kodak XOMAT films with intensifying screens (Kodak, Heidelberg, Germany) at −70° C.

For IgE dot blot experiments, 100 ng of recombinant clone 10-derived allergen and recombinant grass pollen allergens, Phl p 1, Phl p 5, Phl p 7 and Phl p 12, as well as 3 µg of wheat pollen extract and 2 µg of mature wheat seed PBS-extract were dotted onto a nitrocellulose membrane. The nitrocellulose strips were blocked with buffer A and exposed to patients sera at a 1:10 dilution in buffer A over night at 4° C. Bound IgE antibodies were detected with $^{125}I$-labelled anti-human IgE antibodies (RAST RIA, Demeditec Diagnostics, Germany) diluted 1:20 in buffer A over night at room temperature and visualized by autoradiography using Kodak XOMAT films with intensifying screens (Kodak) at −70° C.

MS and CD Analysis of Recombinant Clone 10

Laser desorption mass spectra were acquired in a linear mode with a TOF Compact MALDI II instrument (Kratos, Manchester, UK; piCHEM, Research and Development, Graz, Austria). Samples were dissolved in 10% acetonitrile (0.1% trifluoroacetic acid), and α-cyano-4 hydroxycinnamic acid (dissolved in 60% acetonitrile, 0.1% trifluoroacetic acid) was used as a matrix. For sample preparation a 1/1 mixture of protein and matrix solution was deposited onto the target and air-dried.

CD measurements were performed with purified clone 10-derived allergen (in $H_2O$) at a protein concentration of 0.1 mg/ml on a Jasco J-810 spectropolarimeter (Tokyo, Japan) using a 0.2 cm path length rectangular quarz cuvette. Far-UV CD spectra were recorded from 190 nm to 260 nm with 0.5 nm resolution at a scan speed of 50 nm/min and resulted from the average of three scans. Results are expressed as the mean residue ellipticity (θ) at a given wavelength. Temperature scans were performed according to a step-scan procedure, where the sample was heated from 25° C. to 95° C. with a heat rate of 2° C./min and cooled back to 25° C. at the same rate. Every 5° C. continuous wavelength spectra were recorded with the specified parameters. In addition, temperature scans were recorded at 215 nm with a step resolution of 0.5° C. Results are expressed as the molar mean residue ellipticity ($θ_{MRE}$) at a given wavelength. The final spectra were corrected by subtracting the corresponding baseline spectrum obtained under identical conditions. The secondary structure content of clone 10-derived allergen was calculated using the secondary structure estimation program CDSSTR (9).

Human Rat Basophil Leukaemia (huRBL) Assay

For the quantification of IgE Ab-mediated, immediate-type reactions, huRBL cell mediator release assays were performed. RBL cells (clone RBL-703/21) transfected with the human FcεRI (10) were cultured in RPMI 1640 supplemented with 5% FCS, 4 mM L-Glutamine, and 1 mg/ml G418 sulfate. Cells were harvested after incubation with Trypsin/EDTA, washed, re-suspended in culture medium, and the cell concentration was adjusted to $2×10^6$ cells/ml. Fifty µl aliquots of the cell solution were added to the wells of a 96-well flat-bottom microplate (cell density/well was $1×10^5$ cells). Human sera were diluted 1:10 in culture medium, added to the cells and incubated overnight at 37° C., 7% $CO_2$, 95% relative humidity. Medium was removed and the plates were washed 3 times with 200 µl/well of Tyrode's buffer+0.1% BSA. For IgE cross-linking, 100 µl of clone 10-derived allergen or rPhl p 1, (0.3 µg/ml), diluted in Tyrodes's buffer containing 50% $D_2O$ and 0.1% (w/v) BSA were added to the cells. For spontaneous release, Tyrodes' buffer without protein was added to the wells. Total release was determined by addition of Tyrode's buffer containing 10% Triton X-100. After incubation at 37° C., 7% $CO_2$, 95% relative humidity for 1 hour cells were harvested by centrifugation and 50 μl supernatant was transferred to a new plate, and 50 μl assay solution (0.1M Citric Acid or Sodium Citrate, pH 4.5 and 160 μM 4-methyl umbelliferyl-N-acetyl-β-D-glucosaminide) per well was added. After another one hour incubation the reaction was stopped by adding 100 μl glycine buffer (0.2M glycine, 0.2% NaCl, pH 10.7) to each well. Fluorescence was measured at $\lambda_{ex}$: 360/$\lambda_{em}$: 465 in a fluorescence microplate reader. Spontaneous release was determined from control wells that had not been lysed by Triton X-100. Specific release was calculated using the formula: (sample-spontaneous/total-spontaneous)×100.

Immunogold Electron Microscopy

Dry grains of wheat were cut into small pieces (cubes of approximately 0.5 mm size) using a sharp razor blade. In order to preserve the dry state of the cells, the cubes were anhydrously fixed in acrolein vapor for 5 days at room temperature. They were transferred at room temperature for 1 day to dimethoxypropane (DMP) for removing any residual water and embedded into Lowicryl K4M resin using ascending series of DMP:ethanol and ethanol:monomeric Lowicryl K4 M as intermediate stages. Polymerization was performed at −35° C.

Ultrathin sections were cut from both peripheral and central grain tissues and placed on silver grids for immunolabeling procedures.

Labelling for clone 10-derived allergen was performed in a moist chamber at room temperature (PBS buffer+1% (w/v) BSA, pH 7.4, Tris buffer+1% (w/v) BSA, pH 8.2) as follows: 1.5% (w/v) BSA in PBS buffer, 15 minutes; 2. rabbit anti-wheat protein 10 antibodies and pre-immune antibodies, diluted 1:35 in PBS buffer, 2 hours; 3. PBS buffer, 5 minutes, Tris buffer, 2×5 minutes; 4. goat anti-rabbit IgG antibodies coupled to colloidal gold particles of 10 nm size (BioCell, Plano, Wetzlar, Germany), diluted 1:20 in Tris buffer; 5. Tris buffer, 1×5 minutes, distilled water, 2×5 minutes.

Sections were stained using uranyl acetate (5 minutes) and lead citrate (10 seconds).

Samples were analyzed in a transmission electron microscope EM 410 (FEI, Eindhoven, The Netherlands).

Results

Isolation and Characterization of a Wheat cDNA Coding for a Serine Proteinase Inhibitor-Like Allergen A wheat seed cDNA expression library was screened with IgE antibodies from four patients suffering from bakers' asthma. The open reading frame of the cDNA of the IgE-reactive clone 10 contained 262 nucleotides coding for a 84 amino acids polypeptide (FIG. 1). A molecular mass of 9.4 kDa and an isoelectric point (pI) of 6.08 was calculated according to the deduced amino acid sequence for the clone 10-derived allergen. The analysis of amino acid composition showed a high content of valin residues (15.5%) and absence of cysteine residues. According to computer-aided secondary structure analysis the clone 10-derived allergen consists mainly of random coils and beta-sheets and one alpha-helical domain. According to solvent accessibility calculations almost 80% of the amino acids are solvent exposed. A search for sequence motifs revealed the presence of one potential casein kinase II phosphorylation site (amino acid 32), two N-terminal myristoylation sites (amino acids 11, 55) and a potato inhibitor I family signature (FIG. 1: amino acids 25-36 are boxed). A comparison of the clone 10-derived amino acid sequence with sequences deposited in the NCBI database showed that the allergen is almost identical to a *Triticum aestivum* subtilisin-chymotrypsin inhibitor WSCI precursor (accession no. gi|122065237) and to *T. aestivum* WSCI proteinase inhibitor (accession no. gi|66356278) and exhibits significant sequence homologies with a group of serine proteinase inhibitors occurring in plants and animals. These serine proteinase inhibitors constitute a family designated potato inhibitors I and are characterized by a typical consensus sequence pattern which is conserved in each of the proteins. The serine proteinase inhibitors belonging to the potato inhibitor I family are small proteins of 60-90 amino acids lacking disulphide bonds and contain only a single inhibitory site. The sequences of wheat serine proteinase inhibitors show a significant degree of sequence conservation to proteinase inhibitors of other monocotyledonic plants like barley (*Hordeum vulgare*), maize (*Zea mays, Zea diploperennis*), gamma grass (*Tripsacum dactyloides*) and rice (*Oryza sativa*), dicotyledonic plants and worms (Table III). Table III displays the percentages of sequence identities between each of the serine proteinase inhibitors.

Expression, Purification and Physicochemical Characterization of the Serine Proteinase Inhibitor-Like Allergen The clone 10-derived allergen was expressed in *E. coli* BL21 (DE3) with a C-terminal hexahistidine tag. Approximately 25 mg/L liquid culture of serine proteinase inhibitor-like allergen could be purified by nickel chromatography (FIG. 2A). MALDI-TOF analysis of purified recombinant protein 10 resulted in a mass peak of 9970.8 Da (FIG. 2B). The far-UV CD spectrum of purified recombinant clone 10-derived allergen (FIG. 2C) indicates that the protein is folded and contains a considerable amount of β-sheets and a low α-helical content. The spectrum is characterized by a minimum at 204 nm and a maximum at 190 nm. Secondary structure analysis using the program CDSSTR with the reference dataset 7 yielded 8% α-helix, 23% β-sheets, 14% β-turns and 53% random coils. The NRMSD value of 0.033 demonstrated a good fit between the calculated and the experimentally derived spectra. Upon heating to 95° C. a slight shift of the minimum of the CD spectrum (from 204 nm to 201 nm) was observed, indicating a partial denaturation of the protein. Upon cooling to 25° C. the protein refolded (FIG. 2C). However, the minimum at 204 nm was lower than before heating, which suggests a rearrangement of the β-sheets. In summary, the spectra observed during the temperature scan point to a high thermal stability of the clone 10-derived allergen.

Recombinant Clone 10-Derived Allergen is a New Serine Proteinase Inhibitor-Like Allergen from Wheat Purified clone 10-derived allergen was tested for IgE reactivity using sera from patients suffering from bakers' asthma, grass pollen allergy and food allergy to wheat by dot blot analysis (FIG. 3). The recombinant clone 10-derived allergen reacted with IgE-antibodies from 3 (#1, #4, #12) out of 22 patients suffering from bakers' asthma (13.6%). Patient #1 who had only low IgE levels specific for the major wheat allergen, alpha amylase inhibitor, showed strong IgE reactivity to the serine proteinase inhibitor-like allergen. Interestingly, the clone 10-derived allergen was exclusively recognized by IgE antibodies from patients with baker's asthma but not by patients suffering from IgE-mediated food allergy to wheat or patients suffering from grass pollen allergy. Several sera from each of the three patients groups showed IgE reactivity to recombinant timothy grass pollen allergens due to co-sensitization to grass pollen. The specific IgE reactivity of the clone 10-derived allergen by baker's asthma patients was confirmed in a chip analysis using additional 20 sera from celiac disease patients, 119 food allergic patients, 23 sera from grass pollen allergic patients and 25 baker's asthma patients (Constantin et al, unpublished, data not shown).

The analysis of IgG subclass reactivities to the clone 10-derived allergen in the group of baker's asthma patients showed the presence allergen-specific $IgG_1$ and to a lower extent of allergen-specific $IgG_4$ levels both indicative of a $Th_2$ response whereas no relevant $IgG_2$ and $IgG_3$ reactivity specific for the clone 10-derived allergen was detected (FIG. 4).

To study the allergic activity of IgE antibodies specific for the serine proteinase inhibitor-like allergen RBL cells expressing the human FcεRI were loaded with serum IgE from patients with and without specific IgE antibodies and subsequently exposed to the allergen (FIG. 5). RBL cells loaded with serum IgE from patient #1 showed the strongest degranulation upon allergen exposure (51% of total β-hexosaminidase release). A lower degranulation was obtained with RBL cells that had been loaded with IgE from patients #4 and #12 (22% and 19%, respectively) which corresponded with the intensity of IgE recognition in the dotblots (FIG. 3). Almost no degranulation was observed when RBL cells were loaded with serum from a non-allergic person (FIG. 5: NC). The major timothy grass pollen allergen rPhl p 1 induced strong degranulation in RBL cells loaded with serum IgE from patient #12 and mild degranulation when RBL cells were loaded with sera from patients #1 and #4 (FIG. 5). In fact, patients #1, #4 and #12 suffered also from grass pollen allergy (Table I).

The Serine Proteinase Inhibitor-Like Allergen Accumulates in Wheat Seeds During Maturation Rabbit antibodies, specific for clone 10-derived allergen, were used to investigate the expression of the protein during wheat seed maturation (FIG. 6). Nitrocellulose sheets containing extracts from wheat seeds collected at different time points of seed maturation were probed with specific rabbit antibodies and the pre-immune Ig. The clone 10-specific antibodies reacted with a protein of 40 kDa, representing a tetramer of the serine proteinase inhibitor-like allergens (FIG. 6) (11). The expression of the protein became detectable in 15 days old seeds and continued to increase during further maturation of seeds (FIG. 6). No immunoreactivity was found when the blots were incubated with the pre-immune Ig from the same rabbit (FIG. 6).

The Serine Proteinase Inhibitor-like Allergen is Preferentially Detected in Wheat Seeds When we compared pollen and seeds, we found that the serine proteinase inhibitor-like allergen is preferentially expressed in seeds (FIG. 7) whereas only a weak signal was obtained at approximately 65 kDa in wheat pollen extract. The panallergen profilin was detected with rabbit anti-wheat seed profilin antibodies in wheat seeds and pollen (FIG. 7: #123). No reactivity was found with pre-immune Ig (FIG. 7).

Next we used the serine proteinase inhibitor-like allergen-specific antibodies to search for cross-reactive structures in rice, maize, common bean and potato for which homologous proteins have been described with a sequence identity of 50% (bean), 49% (maize, rice) and 33% (potato) (Table III).

The serine proteinase inhibitor-like allergen was detected again as tetramer in wheat seeds, a band of approximately 23 kDa was detected in rice but no reactivity was found in maize, common bean or potato (FIG. 8C) although comparable amounts of each extract had been subjected to SDS-PAGE (FIG. 8A). No reactivity was observed when the blots were incubated with the pre-immune Ig (FIG. 8B).

Localization of the Serine Proteinase Inhibitor-like Allergen in the Aleurone Layer and Between Starch Granules of a Wheat Grain by Immunogold Electron Microscopy FIG. 9A shows an ultra-thin section through a wheat grain at low magnification in the transmission electron microscope. Three major morphological components of the grain are visible: an outward multi-layered fruit and seed coat (C), the aleuron layer (AL) and the beginning of the voluminous interior of the grain, the starchy endosperm (SE). The rectangle marks an area comparable to the area shown in B. FIG. 9B displays the border between an aleuron cell and the adjoining starchy endosperm at higher magnification. The aleuron cell is filled with aleuron grains (AG) (protein vacuoles) which are surrounded by small lipid vesicles (L). Both components are embedded in the cytoplasmic matrix of the cell. The starchy endosperm consists of starch granules with variable size, closely packed just leaving small interspaces of amorphous cytoplasmatic material. The rectangles indicate areas shown in high magnification in C, D and E, F, respectively. FIG. 9C shows the localization of clone 10-derived allergen in an aleuron cell using Abs raised against wheat protein 10. Gold particles (arrows) indicate the presence of wheat protein 10 predominantly in the cytoplasmatic matrix between cell organelles but also in the peripheral parts of the lipid vesicles (L). In the starch region, wheat protein 10 is associated with the amorphous cytoplasmatic material (CY) in between the starch granules (SG) (FIG. 9E). Control experiments with preimmune Abs showed a very low degree of non-specific labelling (FIGS. 9, D and F).

EXAMPLE 2

Expression and Purification of Recombinant Allergens

Example 2 shows the identification and characterization of six IgE reactive wheat seed allergens named clones #10, #37, #38, #112, #123 and #126. Furthermore Example 2 shows a method for expression and purification of recombinant allergens of said clones.

Biological Materials, Patients' Sera Wheat seeds from *Triticum aestivum* cv. Michael were obtained from the Österreichische Agentur für Gesundheit und Ernährungssicherheit GmbH and planted in a glasshouse. Immature seeds were harvested directly into liquid nitrogen after a period of 25 days until pollination started and stored at −80° C. until use. Sera were obtained from 24 patients suffering from bakers' asthma (Table IV). Baker's asthma was diagnosed on the basis of case history, total serum IgE levels, IgE specific for wheat and rye by CAP-FEIA System (Phadia, Uppsala, Sweden) and after specific inhalation challenge tests (1) (FIG. 10). Serum from grass pollen allergic patients had been analyzed for total serum IgE levels and IgE specific timothy grass pollen by CAP-FEIA System (Phadia) and food allergic patients to wheat have been characterized as described previously (2) (FIG. 11). Clinical data of these patients are summarized in table V. For control purposes serum from a non-allergic individual was included in the experiments.

Construction of a λgt11 cDNA Library from Wheat Seeds

Total RNA was extracted from wheat seeds stored at −80° C. according to Yeh [3]. Then the RNA pellet was dissolved in guanidinium isothiocyanate buffer (4M guanidinium isothiocyanate, 0.83% v/v 3M sodium acetate, pH 6, 0.11M β-mercaptoethanol) and purified by a cesium chloride density gradient ultracentrifugation. Poly-A$^+$ RNA was isolated by oligo-dT cellulose affinity chromatography (Nucleo Trap mRNA; Machery-Nagel) and double stranded cDNA was synthesized via a cDNA synthesis kit (cDNA synthesis System; Roche Diagnostics, Mannheim, Germany). After methylation with EcoRI methylase (New England Biolabs, Beverly, Mass.), EcoRI linkers (New England Biolabs) were added to the cDNA. Linkered cDNA was digested with EcoRI (Roche Diagnostics). Digested linkers were removed with a Nick column (Pharmacia Biotech, Uppsala, Sweden) and the cDNA was ligated into λgt11 arms (Stratagene, La Jolla, Calif., USA). The ligation product was packed in vitro (Gigapack III Gold Cloning Kit, Stratagene) resulting in a λgt11 expression cDNA library with 2.43×10$^6$ PFU (plaque forming units).

Isolation and Characterization of IgE-reactive Clones from a Wheat Seed cDNA Library E. coli Y1090 were infected with 7×10$^5$ PFU of recombinant phages and immunoscreened with serum IgE of four patients (#1, #2, #5, #13) suffering from bakers' asthma as described [5]. Six IgE-reactive phage clones were selected for further re-cloning and their DNA was PCR-amplified using Platinum PCR Supermix (Invitrogen, Life Technologies) with λgt11 primers and sequenced (MWG, Ebersberg, Germany). The obtained sequences were compared with sequences submitted to the GenBank database at the National Center for Biotechnology Information (NCBI).

Expression and Purification of Recombinant Allergens

The coding region of the clones were amplified by PCR using primers listed in table VI. The PCR products were subcloned into an AccepTor Vector (Novagen, Madison, Wis.) and sequenced again (MWG). Then the insert containing AccepTor Vectors were digested with NdeI and EcoRI (Roche Diagnostics), the inserts were gel-purified (Promega, Madison, Wis., USA) and subcloned into the expression plasmid pET 17b (Novagen). The DNA sequences were confirmed by sequencing both DNA strands (Microsynth, Balgach, CH). The pET 17b-insert constructs were transformed into E. coli BL21 (DE3) (Stratagene) and grown in Luria Broth (LB) medium containing 100 mg/l ampicillin at 37° C. to an OD (600 nm) of 0.8-1. Protein expression was induced by addition of isopropyl β-D-thiogalactopyranoside (IPTG) to a final concentration of 0.5 mM and growing the bacteria for additional 3 h. Then bacteria were harvested by centrifugation and homogenized in 25 mM imidazole, pH 7.5, 0.1% (v/v) Triton X-100 with an Ultraturrax (IKA, Stauffen, Germany). DNA was digested by addition of DNase I, stirred for additional 10 min at 20° C., stopped with 200 µl of 5M NaCl and then centrifuged at 4° C. (6000g, 20 min). Clone 10-derived allergen was purified from the inclusion body-containing pellet under denaturing conditions over Ni-NTA resin affinity columns according to the QIAexpressionist handbook, protocol 17 (QIAGEN, Hilden, Germany). Fractions containing the recombinant allergen were pooled and dialyzed against 10 mM NaH2PO4 pH 7.5. Recombinant proteins #37, #38, #112, #123 and #126 were purified from the pellet of the bacterial cell lysate under native conditions over Ni-NTA resin affinity columns according to the QIAexpressionist handbook, protocol 12 (QIAGEN). Fractions containing the recombinant proteins were pooled and dialyzed against 10 mM NaH2PO4 pH 7.5. Protein samples were analyzed for purity on a 14% SDS-PAGE gel and visualized by Coomassie brilliant blue staining. The protein concentrations were determined with Micro BCA Protein Assay Kit (Pierce, Rockford, Ill.).

EXAMPLE 3

Allergen Array

Example 3 shows an allergen micro-array revealing that recombinant wheat seed allergens, prepared as described in example 2, are specifically recognized by serum IgE from baker's asthma patients but not from patients with food allergy to wheat or grass pollen allergy. Hence the recombinant allergens are specific for respiratory allergy to wheat flour. Moreover Example 3 shows the use of timothy grass pollen marker allergens phl p 1 and Phl p 5 and wheat pollen in the array for improvement of in vitro diagnosis of respiratory allergy.

Techniques

Patients and Sera

Sera were obtained from Spanish patients suffering from baker's asthma (B1-B23), Austrian (F1-F26) and German patients (F27-F38) suffering from wheat induced food allergy and Austrian patients (G1-017) suffering from grass pollen allergy. Patients were selected according to a positive case history, specific inhalation challenge tests for confirmation of a clinically relevant sensitization in case of baker's asthma (1) and double blind placebo controlled food challenge (DB-PCFC) in infant patients with food allergy to wheat. Serum from all patients has been analyzed for total serum IgE levels and IgE specific for wheat flour and timothy grass pollen by the CAP-FEIA System (Phadia, Uppsala, Sweden). Demographic, clinical and serological data of these patients are summarized in Table VII, VIII and IX. For control purposes, sera from healthy individuals were included in all experiments.

Biological Materials

Recombinant wheat proteins #10, #37, #38, #112, #123 and #126 derived from a cDNA library by screening with sera from baker's asthma patients were expressed in E. coli and purified as described (12). Wheat pollen were purchased from Allergon (Vällinge, Sweden) and recombinant Phl p 1, Phl p 5, Phl p 7, Phl p 12 from BIOMAY (Vienna, Austria).

Protein Extract

Triticum aestivum pollen (500 mg) was extracted at 4° C. over night in 5 ml PBS, 2 mM EDTA, 1 mM PMSF. After centrifugation for 1 h at 13,000×g 4° C., the protein concentration of the supernatant was determined with Micro BCA Protein Assay Kit (Pierce, Rockford, Ill.) and aliquots were stored at −20° C. until use.

Allergen Microarray Analysis

Wheat pollen extract, 1-1.5 ng/spot, recombinant and purified wheat proteins and recombinant grass pollen allergens, 0.1-0.15 ng/spot, were spotted with a Nano Plotter NP2 (Gesellschaft für Silizium-Mikrosysteme mbH, GroBerkmannsdorf, Germany) on nitrocellulose membranes that were attached to microscope glass slides as described (13). Purified human IgE was used as a position marker (14). The spotted microarrays were pre-washed with 30 µl assaybuffer (weak phosphate buffer, pH 7.5) and incubated with 30 µl undiluted sera from allergic patients or controls. After washing with 30 µl assaybuffer bound IgE antibodies were detected with 20 µl fluorophore-conjugated anti-IgE antibody and fluorescence intensities (FI) were measured at a wavelength of 635 nm (GenePix 4000B fran Axon). The cut off level was set to FI=300 based on values obtained with human serum albumin.

Results

Description of Patients

We analyzed patients suffering from baker's asthma, wheat-induced food allergy or grass pollen allergy. The group of baker's asthma patients consisted of 23 persons (4 females, 19 males: mean age 39 years, range 22-60 years) with occupational exposure to wheat flour. Ninety-one percent of the baker's asthma patients suffered from asthma due to inhalation of wheat flour and 94% complained about symptoms of rhinoconjunctivitis. A sensitization to other respiratory allergen sources (e.g., cat, cockroach, dog, grass pollen, horse, house dust mites, moulds and/or olive pollen) was found in 70% of the baker's asthma patients and 48% of the patients suffered from grass pollen allergy (Table VII). Interestingly, none of the baker's asthma patients exhibited allergy to food and symptoms were confined to respiratory manifestations.

The group of patients suffering from wheat-induced food allergy comprised 38 individuals (25 females, 13 males: mean age 13 years, range 0.5-65 years) (Table VIII). Again we found that 71% are sensitized to other respiratory allergen sources (e.g., birch pollen, grass pollen, house dust mites and mugwort pollen) and 58% were also sensitized to food allergens (e.g., carrot, cow's milk, hazelnut, hen's egg, malt, nuts, orange, plum, rice, soybean, celery, seafood, shrimps and/or spices) (Table VIII). IgE-mediated sensitization to grass pollen was found in 55% of these patients. The symptoms of these patients varied from respiratory symptoms (e.g., asthma, bronchitis, cough, conjunctivitis, dyspnea, nasal congestion, rhinorrhoe, rhinoconjunctivitis) to gastrointestinal symptoms (e.g., abdominal pain, diarrhoea, flatulence, sore throat and vomiting) and cutaneous symptoms (e.g., eczema, pruritus and urticaria) (Table VIII).

The group of grass pollen allergic patients consisted of 17 patients (5 females, 12 males: mean age 13 years, range 0.5-65 years). Seventy one percent of these patients suffered also from allergy to other respiratory allergen sources (e.g., birch pollen, cat, dog, house dust mites, rabbit and mugwort pollen) (Table IX). According to serology 65% exhibited IgE reactivity to wheat flour and 23% contained IgE against other food allergens. However, only one patient suffered from urticaria and no symptoms of food allergy could be recorded for these patients. Respiratory symptoms such as asthma, conjunctivitis, dyspnea, rhinoconjunctivitis and rhinitis dominated in the grass pollen allergic patients.

Composition of the Allergen Array

Six recombinant wheat seed allergens designated as #10, #37, #38, #112, #123 and #126 were spotted onto nitrocellulose-coated glass slides (FIG. 12, A). The recombinant wheat proteins were expressed in *Escherichia coli* based on cDNAs which had been isolated from a wheat seed cDNA library with sera from baker's asthma patients as described (15). According to homology with sequences deposited in the NCBI database the wheat allergens can be described as follows: #10 has a 96% homology to a *Triticum aestivum* subtilisin-chymotrypsin inhibitor WSCI precursor (accession no. gi|122065237), #37 is a *T. aestivum* thioredoxin H (accession no. gi|27461140), #38 is a *T. aestivum* glutathione transferase (accession no. gi|20067419), #112 has a 99% homology with a *T. aestivum* 1-Cys-peroxyredoxin (accession no. gi|34539782), #123 has a 96% homology with *T. aestivum* profilin (accession no. gi|1346803) and #126 has a 69% homology with *Hordeum vulgare* dehydrin 11 (accession no. gi|4105101).

In addition to the recombinant wheat allergens, wheat pollen extract, recombinant timothy grass pollen allergens (rPhl p 1, rPhl p 5, rPhl p 7 and rPhl p 12) (16-19) and IgE were also spotted onto the slides (FIG. 12, A). Representative images of allergen microarrays after incubation with sera are shown in FIG. 12, B-C. On the chip probed with serum from a nonallergic person showed no reactivity with any allergen could be detected and only the spotted IgE markers were detected with the anti-IgE conjugate (FIG. 12, B). Figures in 12, C show representative images of microarray chips incubated with sera from a baker's asthma patient (1), a patient suffering from wheat-induced food allergy (2) and a grass pollen allergic patient (3). The baker's asthma patient (1: Table I: B4) shows strong IgE reactivity to recombinant wheat allergens #10 and weak reactivities to #126 and #112. For the food allergic patient (2: Table VIII: F26) strong IgE binding to recombinant profilin from wheat #123 and timothy grass pollen rPhl p 12 and weak binding to wheat pollen extract and rPhl p 1 was observed. The image of the chip from a grass pollen allergic patient (3: G16) shows strong signals to rPhl p 5 and rPhl p 12 and weaker signals with wheat profilin #123, wheat pollen extract and rPhl p 1.

Identification of Wheat Seed Allergens Specifically Recognized by IgE Antibodies from Baker's Asthma Patients Ninety one percent of the baker's asthma patients were positive in the wheat flour CAP (Table VII). Using spotted wheat allergens the IgE reactivity profile for 62% of the baker's asthma patients could be established. Allergens #126 (30%), #10 (26%), #123 (22%) and #122 (17%) were the most frequently detected components whereas #37 and #38 reacted only with 4% of the sera (FIG. 13, A). Interestingly, the two patients who were negative in the wheat flour CAP (B5, B18: Table VII) reacted with allergen #126. Forty eight percent of the baker's asthma patients showed IgE reactivity to timothy grass pollen extract and each of these patients was also diagnosed with a combination of spotted rPhl p 1 and rPhl p 5. Recombinant Phl p 12 (35%) was always stronger and more often recognized than wheat profilin #123 (22%). The cross-reactive pollen allergen rPhl p 7 reacted with 13% of the sera.

Recombinant Wheat Seed Allergens Recognized by Baker's Asthma Patients are not Targets for IgE Antibodies of Patients Suffering from Wheat-Induced Food Allergy All patients with food allergy to wheat were positive in the wheat flour CAP but the recombinant wheat proteins were hardly recognized (5%) (FIG. 13, B). The two patients who were positive to cross-reactive timothy grass pollen profilin, had also a positive signal to wheat profilin #123 in the microarray. Fifty five percent of patients with wheat induced food allergy showed IgE reactivity in the *Phleum* CAP but just 18% were positive to wheat pollen extract on the chip and 26% in the combination of spotted rPhl p 1 and rPhl p 5. Spotted rPhl p 1 and rPhl p 5 alone were recognized by 18% and 16% of the sera respectively, the cross-reactive allergens rPhl p 7 and rPhl p 12 reacted with 13% and 26% of the sera.

rPhl p 1 and rPhl p 5 are Diagnostic Marker Allergens for Grass Pollen Allergy Whereas Profilin is Recognized by Baker's Asthma and Wheat Food Allergic Patients Sixty-five percent of grass pollen allergic patients were positive in the wheat flour CAP. Out of the recombinant wheat proteins tested in the microarray, only recombinant wheat protein #123 was recognized by 23.5% of the patients (FIG. 13, C). Each of these patients were also positive to cross-reactive timothy grass pollen profilin rPhl p 12. But rPhl p 12 was always stronger and more often (35%) recognized than #123. All patients suffering from grass pollen allergy were positive on the timothy grass pollen CAP and in the combination of spotted rPhl p 1 and rPhl p 5. Recombinant Phl p 1 alone was more often recognized (94%) than rPhl p 5 (88%) by patients with grass pollen allergy. Wheat pollen extract reacted with 82% of the sera and cross-reactive rPhl p 7 with 29%.

All grass pollen allergic patients and baker's asthma patients with grass pollen allergy were positive in the combination of rPhl p 1 and rPhl p 5 in the microarray and in the *Phleum* CAP (FIG. 13, A; C). These findings are in agreement with previously published data showing that grass pollen allergy can be diagnosed by IgE reactivity to rPhl p 1 and rPhl p 5 (20, 21). However, among patients with wheat induced food allergy only 26% reacted with rPhl p 1 and rPhl p 5 in the microarray, but more than twice as many (55%) were positive in the *Phleum* CAP (FIG. 13, B). Furthermore, those patients reacting with grass pollen extract in the CAP system and with timothy grass pollen profilin (rPhl p 12) in the microarray were also positive to wheat profilin (22) due to cross-reactivity of plant profilins (23). Nevertheless, frequency and intensity of IgE recognition was always stronger to rPhl p 12 than to wheat profilin (22).

EXAMPLE 4

The analyte is immobilized to a solid support, such as ImmunoCAP (Phadia, Uppsala, Sweden). Serum samples from at least three representative human patients sensitized to the allergen and showing IgE reactivity to that allergen are incubated for 3 h at room temperature with the allergen at a final concentration of 100 µg/mL and, in parallel as negative controls, with buffer alone and the non-allergenic maltose binding protein (MBP) of *E. coli*. The samples are then analysed for IgE binding to ImmunoCAP (Phadia, Uppsala, Sweden) tests carrying immobilized analyte to study whether preincubation with allergen specifically inhibits or significantly lowers IgE binding.

TABLE I

Demographic, clinical and serological characteristics of patients suffering from bakers' asthma

| Patients | Age | Sex | Asthma | occupational exposure | IgE conc. kUA/l Wheat | Rye | Soybean | fungal α-Amylase | SPT to grass pollen | total IgE kU/l | PC20 | mg/ml |
|---|---|---|---|---|---|---|---|---|---|---|---|---|
| 1 | 35 | m | + | + | 74.2 | 20.7 | n.d. | 0.63 | + | 163 | + | 0.29 |
| 2 | 29 | m | + | + | 18 | 7.9 | 6.1 | 1.5 | + | 271 | + | 2 |
| 3 | 36 | m | + | + | 1.66 | 1.24 | <0.35 | <0.35 | − | 353 | + | 0.31 |
| 4 | 39 | m | + | + | 25.8 | 15.6 | 1.36 | 18.6 | + | 1387 | + | 0.25 |
| 5 | 54 | m | + | + | <0.35 | <0.35 | <0.35 | 3.21 | − | 30.1 | | n.d. |
| 6 | 35 | m | + | + | 24.3 | 39.6 | 5.73 | 2.29 | + | 416 | + | 0.25 |
| 7 | 28 | m | + | + | 2.58 | 3.77 | <0.35 | 5.39 | + | 248 | + | 0.25 |
| 8 | 27 | m | + | + | 7.86 | 7.4 | 3.19 | 32.2 | + | 1773 | + | 0.47 |
| 9 | 24 | m | − | + | 2.35 | 2.32 | 1.62 | n.d. | + | 204 | + | 0.09 |
| 10 | 60 | m | + | + | 3.44 | 4.08 | <0.35 | 1.15 | + | 73.3 | + | 0.44 |
| 11 | 22 | m | + | + | 3 | 2 | <0.35 | <0.35 | − | 2509 | + | 3.38 |
| 12 | 26 | m | + | + | >100 | >100 | 10.7 | 7.63 | + | 321 | + | 0.5 |
| 13 | 54 | m | + | + | 2.48 | 0.6 | 0.71 | <0.35 | − | 480 | + | 0.12 |
| 14 | 60 | m | + | + | 31.8 | 31.1 | n.d. | <0.35 | + | 629 | + | 0.15 |
| 15 | 27 | m | + | + | 5.06 | n.d. | n.d. | <0.35 | + | 278 | + | 0.079 |
| 16 | 42 | f | + | + | 3.71 | 2.71 | 1.69 | <0.35 | + | 271 | + | 0.187 |
| 17 | 54 | m | + | + | 1.68 | 1.13 | <0.35 | <0.35 | − | 79.2 | + | 16 |
| 18 | 59 | m | + | + | <0.35 | <0.35 | <0.35 | 5 | − | 673 | + | 0.23 |
| 19 | 26 | m | + | + | 74.6 | 58.4 | <0.35 | <0.35 | + | 17.7 | + | 1.16 |
| 20 | 43 | m | + | + | 13.8 | 26.9 | 0.77 | <0.35 | + | 538 | + | 0.25 |
| 21 | 34 | f | + | + | 2.05 | 1 | <0.35 | <0.35 | + | n.d. | + | 0.5 |
| 22 | 41 | f | + | + | 1.77 | 0.75 | <0.35 | <0.35 | + | 23.4 | + | 0.23 | m: male, f: female,
+: positive, −: negative,
n.d.: not done,
kUA/l—kilounit antigen per liter,
SPT: skin prick test,
PC20: Methacholine inhalation challenge

TABLE II

Demographic, clinical and serological characteristics of patients suffering from food allergy to wheat and grass pollen allergy

| Patients | Age | Sex | RC | AD | Asthma | IgE conc. kUA/l Wheat | Rye | total IgE kU/l |
|---|---|---|---|---|---|---|---|---|
| F1 | 34 | f | − | + | + | 18.6 | 13.4 | >2000 |
| F2 | 34 | m | + | − | − | 3.1 | 3.08 | 155 |
| F3 | 24 | f | − | + | − | 1.3 | n.d. | 336 |
| F4 | 15 | f | − | + | − | 5.91 | 5.3 | 915 |
| G1 | 45 | m | + | − | + | 1.76 | 2 | 175 |
| G2 | 39 | m | + | − | + | 11.1 | 10.3 | 401 |
| G3 | 55 | f | − | − | − | 3.16 | 1 | 157 |
| G4 | 54 | m | + | − | + | n.d. | n.d. | 1528 |

F: food allergy, G: grass pollen allergy,
m: male, f: female,
RC: rhinoconjunctivitis,
AD: atopic dermatitis,
+: positive, −: negative,
n.d.: not done,
kUA/l—kilounit antigen per liter

TABLE III

Percentage amino acid sequence identities

| | Clone #10 (%) | #1 (%) | #2 (%) | #3 (%) | #4 (%) | #5 (%) | #6 (%) | #7 (%) | #8 (%) | #9 (%) | #10 (%) | #11 (%) | #12 (%) | #13 (%) | #14 (%) | #15 (%) |
|---|---|---|---|---|---|---|---|---|---|---|---|---|---|---|---|---|
| Clone #10 | 100 | 98 | 94 | 85 | 54 | 49 | 49 | 52 | 43 | 43 | 35 | 50 | 43 | 41 | 32 | 35 |
| #1 | | 100 | 97 | 88 | 55 | 50 | 50 | 53 | 44 | 44 | 35 | 50 | 44 | 41 | 32 | 36 |
| #2 | | | 100 | 84 | 52 | 48 | 47 | 50 | 44 | 43 | 33 | 46 | 41 | 40 | 30 | 35 |
| #3 | | | | 100 | 55 | 50 | 50 | 53 | 44 | 44 | 38 | 50 | 44 | 43 | 30 | 40 |
| #4 | | | | | 100 | 88 | 97 | 76 | 35 | 62 | 33 | 50 | 41 | 40 | 27 | 47 |
| #5 | | | | | | 100 | 87 | 73 | 37 | 63 | 33 | 50 | 40 | 40 | 30 | 44 |
| #6 | | | | | | | 100 | 73 | 34 | 50 | 38 | 48 | 48 | 40 | 29 | 45 |
| #7 | | | | | | | | 100 | 36 | 59 | 38 | 46 | 48 | 38 | 38 | 55 |
| #8 | | | | | | | | | 100 | 32 | 41 | 37 | 48 | 48 | 34 | 47 |
| #9 | | | | | | | | | | 100 | 30 | 43 | 35 | 34 | 30 | 39 |
| #10 | | | | | | | | | | | 100 | 43 | 40 | 52 | 40 | 34 |
| #11 | | | | | | | | | | | | 100 | 37 | 46 | 41 | 45 |

TABLE III-continued

Percentage amino acid sequence identities

|  | #12 | #13 | #14 | #15 |
|---|---|---|---|---|
| #12 | 100 | 35 | 37 | 48 |
| #13 |  | 100 | 37 | 38 |
| #14 |  |  | 100 | 35 |
| #15 |  |  |  | 100 |
| #16 |  |  |  |  |
| #17 |  |  |  |  |
| #18 |  |  |  |  |
| #19 |  |  |  |  |
| #20 |  |  |  |  |
| #21 |  |  |  |  |
| #22 |  |  |  |  |
| #23 |  |  |  |  |
| #24 |  |  |  |  |
| #25 |  |  |  |  |
| #26 |  |  |  |  |
| #27 |  |  |  |  |
| #28 |  |  |  |  |
| #29 |  |  |  |  |
| #30 |  |  |  |  |

|  | #16 (%) | #17 (%) | #18 (%) | #19 (%) | #20 (%) | #21 (%) | #22 (%) | #23 (%) | #24 (%) | #25 (%) | #26 (%) | #27 (%) | #28 (%) | #29 (%) | #30 (%) |
|---|---|---|---|---|---|---|---|---|---|---|---|---|---|---|---|
| Clone #10 | 33 | 32 | 34 | 31 | 38 | 35 | 38 | 32 | 48 | 31 | 30 | 30 | 34 | 35 | 28 |
| #1 | 33 | 32 | 34 | 31 | 38 | 35 | 38 | 32 | 48 | 31 | 30 | 30 | 34 | 35 | 28 |
| #2 | 33 | 30 | 32 | 31 | 37 | 35 | 34 | 30 | 43 | 28 | 31 | 28 | 32 | 35 | 27 |
| #3 | 29 | 30 | 32 | 31 | 35 | 35 | 37 | 34 | 43 | 32 | 34 | 31 | 35 | 35 | 30 |
| #4 | 31 | 37 | 37 | 38 | 38 | 42 | 33 | 41 | 44 | 32 | 34 | 30 | 32 | 38 | 30 |
| #5 | 30 | 38 | 45 | 41 | 41 | 45 | 34 | 42 | 44 | 32 | 37 | 33 | 34 | 38 | 25 |
| #6 | 33 | 36 | 45 | 38 | 40 | 44 | 33 | 41 | 43 | 34 | 35 | 38 | 32 | 38 | 30 |
| #7 | 29 | 35 | 35 | 33 | 33 | 33 | 38 | 33 | 40 | 30 | 30 | 27 | 35 | 38 | 27 |
| #8 | 34 | 34 | 37 | 38 | 32 | 40 | 35 | 34 | 38 | 28 | 35 | 37 | 34 | 38 | 37 |
| #9 | 28 | 28 | 28 | 28 | 30 | 33 | 28 | 28 | 33 | 28 | 28 | 23 | 31 | 31 | 24 |
| #10 | 39 | 39 | 31 | 46 | 42 | 54 | 49 | 54 | 48 | 51 | 54 | 57 | 68 | 58 | 51 |
| #11 | 35 | 40 | 69 | 43 | 48 | 41 | 37 | 40 | 79 | 38 | 37 | 30 | 38 | 38 | 33 |
| #12 | 41 | 37 | 34 | 31 | 31 | 34 | 34 | 35 | 40 | 35 | 32 | 34 | 34 | 34 | 32 |
| #13 | 37 | 35 | 41 | 44 | 40 | 40 | 41 | 38 | 47 | 44 | 43 | 35 | 41 | 44 | 37 |
| #14 | 58 | 68 | 25 | 38 | 38 | 39 | 38 | 42 | 40 | 37 | 41 | 37 | 43 | 39 | 38 |
| #15 | 26 | 31 | 38 | 31 | 34 | 41 | 37 | 36 | 49 | 34 | 37 | 31 | 38 | 32 | 35 |
| #16 | 100 | 57 | 27 | 32 | 41 | 42 | 43 | 42 | 35 | 34 | 41 | 38 | 48 | 43 | 38 |
| #17 |  | 100 | 25 | 40 | 42 | 41 | 37 | 44 | 38 | 38 | 44 | 37 | 44 | 42 | 35 |
| #18 |  |  | 100 | 34 | 47 | 39 | 38 | 40 | 80 | 38 | 34 | 31 | 37 | 38 | 31 |
| #19 |  |  |  | 100 | 37 | 58 | 58 | 50 | 48 | 47 | 52 | 53 | 52 | 57 | 42 |
| #20 |  |  |  |  | 100 | 41 | 39 | 35 | 47 | 35 | 34 | 37 | 43 | 42 | 35 |
| #21 |  |  |  |  |  | 100 | 50 | 55 | 44 | 47 | 57 | 48 | 58 | 59 | 50 |
| #22 |  |  |  |  |  |  | 100 | 49 | 40 | 49 | 47 | 55 | 53 | 43 | 55 |
| #23 |  |  |  |  |  |  |  | 100 | 43 | 52 | 50 | 49 | 58 | 51 | 51 |
| #24 |  |  |  |  |  |  |  |  | 100 | 41 | 40 | 33 | 38 | 40 | 35 |
| #25 |  |  |  |  |  |  |  |  |  | 100 | 44 | 50 | 40 | 58 | 45 |
| #26 |  |  |  |  |  |  |  |  |  |  | 100 | 53 | 59 | 58 | 47 |
| #27 |  |  |  |  |  |  |  |  |  |  |  | 100 | 58 | 47 | 80 |
| #28 |  |  |  |  |  |  |  |  |  |  |  |  | 100 | 59 | 81 |
| #29 |  |  |  |  |  |  |  |  |  |  |  |  |  | 100 | 45 |
| #30 |  |  |  |  |  |  |  |  |  |  |  |  |  |  | 100 |

TABLE IV

Bakers' asthma patients

| Patient # | Age at blood donation | Sex | Asthma | occupational exposure | IgE conc. kUA/l Wheat | Rye | Soybean | Amylase | total IgE | PC20 mg/ml |
|---|---|---|---|---|---|---|---|---|---|---|
| 1 | 35 | m | + | + | 74.2 | n.d. | n.d. | 0.63 | 163 | +0.29 |
| 2 | 29 | m | + | + | 18 | n.d. | 6.1 | 1.5 | 271 | +2 |
| 3 | 36 | m | + | + | 1.66 | 1.24 | 0 | 0 | 353 | +0.31 |
| 5 | 39 | m | + | + | 25.8 | 15.6 | 1.36 | 18.6 | 1387 | +0.25 |
| 6 | 54 | m | + | + | 0 | 0 | 0 | 3.21 | 30.1 | n.d. |
| 7 | 35 | m | + | + | 24.3 | 39.6 | 5.73 | 2.29 | 416 | +0.25 |
| 8 | 28 | m | + | + | 2.58 | 3.77 | 0 | 5.39 | 248 | +0.25 |
| 9 | 27 | m | + | + | 7.86 | 7.4 | 3.19 | 32.2 | 1773 | +0.47 |
| 10 | 24 | m | − | + | n.d. | n.d. | n.d. | n.d. | 204 | +0.09 |
| 11 | 60 | m | + | + | 3.44 | 4.08 | 0 | 1.15 | 73.3 | +0.44 |
| 12 | 22 | m | + | + | 3 | 2 | 0 | 0 | 2509 | +3.38 |
| 13 | 26 | m | + | + | >100 | >100 | 10.7 | 7.63 | 321 | +0.5 |
| 14 | 54 | m | + | + | 2.48 | 0.6 | 0.71 | 0 | 480 | +0.12 |
| 15 | 60 | m | + | + | 31.8 | 31.1 | n.d. | 0 | 629 | +0.15 |
| 16 | 27 | m | + | + | 5.06 | n.d. | n.d. | 0 | 278 | +0.079 |
| 17 | 42 | f | + | + | 3.71 | 2.71 | 1.69 | 0 | 271 | +0.187 |
| 18 | 54 | m | + | + | 1.68 | 1.13 | 0 | 0 | 79.2 | +16 |
| 19 | 59 | m | + | + | 0 | 0 | 0 | 5 | 673 | +0.23 |
| 20 | 26 | m | + | + | 74.6 | 58.4 | 0 | 0 | 17.7 | +1.16 |
| 21 | 43 | m | + | + | 13.8 | 26.9 | 0.77 | 0 | 538 | +0.25 |
| 22 | 34 | f | + | + | 2.05 | 1 | 0 | 0 | n.d. | +0.5 |
| 23 | 41 | f | + | + | 1.77 | 0.75 | 0 | 0 | 23.4 | +0.23 |
| 24 | 53 | f | − | − | 0.41 | 2.21 | 0 | 0 | 469 | n.d. |

PC20: Methacholine inhalation challange
m: male, f: female, +: positive, −: negative, n.d.: not done

TABLE V

Food and grass pollen allergic patients

| Patient group | Age at blood donation | Sex | RC | AD | Asthma | IgE conc. kUA/l Wheat | Rye | total IgE |
|---|---|---|---|---|---|---|---|---|
| Food allergic 1 | 32 | m | + | − | − | 3.1 | 3.08 | 155 |
| Food allergic 2 | 34 | f | − | − | + | 18.6 | n.d. | >2000 |
| Food allergic 3 | 24 | f | − | + | − | 1.3 | n.d. | 336 |
| Food allergic 4 | 15 | f | − | + | − | 5.91 | 5.3 | 915 |
| Grasspollen allergic 1 | 45 | m | + | − | + | n.d. | n.d. | n.d. |
| Grasspollen allergic 2 | 39 | m | + | − | + | n.d. | n.d. | 401 |
| Grasspollen allergic 3 | 55 | f | − | − | − | n.d. | n.d. | n.d. |
| Grasspollen allergic 4 | 54 | m | + | − | + | n.d. | n.d. | 1528 | m: male, f: female,
+: positive, −: negative,
n.d.: not done

TABLE VI

PCR Primers used for the amplification of cDNAs

| Primer | Sequence |
|---|---|
| 10 fwd | 5' CAT ATG AGC CCT GTG GTG AAG AAG CCG GAG GGA 3' |
| 10 rev | 5' GAATTC TTA GTG ATG GTG ATG GTG ATG GCC GAC CCT GGG GAC 3' |
| 37 fwd | 5' CAT ATG GCC GCC GAG GAG GGA GCC GTG ATA 3' |
| 37 rev | 5' GAATTC TTA GTG ATG GTG ATG GTG ATG GGC AGA TGC AGA ACC 3' |
| 38 fwd | 5' CAT ATG GCG GGC GAG AAG GGC CTG GTG CTG 3' |
| 38 rev | 5' GAATTC TTA GTG ATG GTG ATG GTG ATG CTC GAT GCC GTA CTT 3' |
| 112 fwd | 5' CAT ATG CCG GGC CTC ACC ATC GGC GAC ACC GTC 3' |
| 112 rev | 5' GAATTC TTA GTG ATG GTG ATG GTG ATG GAC CTT GGT GAA GCG 3' |
| 123 fwd | 5' CAT ATG TCG TGG CAG ACG TAC GTC GAC GAC 3' |
| 123 rev | 5' GAATTC TTA GTG ATG GTG ATG GTG ATG GAA ACC CTG CTC GAC 3' |

TABLE VI-continued

PCR Primers used for the amplification of cDNAs

| Primer | Sequence |
|---|---|
| 126 fwd | 5' CAT ATG GCG GAC TAC GGT GGA GAG TAC GGG 3' |
| 126 rev | 5' GAATTC TTA GTG ATG GTG ATG GTG GTG TCC AGG GAG CTT 3' | fwd: forward; rev: reverse;
Nde I restriction sites are shown in italic letters, Eco RI restriction sites are underlined, hexahistidine-tags are shown in bold letters

TABLE VII

Demographic, clinical and serological characteristics of patients suffering from baker's asthma

| Patient | Sex | Age | Wheat flour IgE kUA/l | *Phleum pratense* IgE kUA/l | Total IgE kU/l | Job | Years exp. | Symptoms | Other allergies | PC20 mg/ml | SIC wheat mg/ml |
|---|---|---|---|---|---|---|---|---|---|---|---|
| B1 | m | 35 | 74.2 | 5.25 | 163 | Confectioner | 20 | A, RC | g | 0.29 | 0.039 |
| B2 | m | 29 | 18 | 53.5 | 271 | Confectioner | 12 | A, RC | g | 2 | n.d. |
| B3 | m | 36 | 1.66 | <0.35 | 353 | Baker | 8 | A, RC | n.k. | 0.31 | n.d. |
| B4 | m | 39 | 25.8 | 0.73 | 1367 | Baker-Confectioner | 20 | A, RC, U | g | 0.25 | n.d. |
| B5 | m | 54 | <0.35 | <0.35 | 30.1 | Baker | 42 | RC, A | n.k. | n.d. | n.d. |
| B6 | m | 35 | 24.3 | 4.67 | 416 | Baker | 12 | RC, A | g | 0.25 | n.d. |
| B7 | m | 28 | 2.56 | <0.35 | 246 | Baker | 14 | A, RC | c, d, h, hdm | 0.25 | n.d. |
| B8 | m | 27 | 7.86 | >100 | 1773 | Baker | 26 | A, RC | n.k. | 0.47 | 0.625 |
| B9 | m | 24 | 2.35 | >100 | 204 | Baker | 18 | RC | c, d, g, h, hdm | 0.09 | n.d. |
| B10 | m | 60 | 3.44 | <0.35 | 73.3 | Confectioner | 46 | A, RC | hdm, m | 0.44 | n.d. |
| B11 | m | 22 | 3 | <0.35 | 2509 | Baker | 5 | A, RC, U | n.k. | 3.36 | 0.0015 |
| B12 | m | 26 | >100 | >100 | 321 | Baker-Confectioner | 5 | A, RC | g | 0.5 | n.d. |
| B13 | m | 54 | 2.48 | <0.35 | 480 | Confectioner | 25 | A, RC | n.k. | 0.12 | n.d. |
| B14 | m | 60 | 31.8 | <0.35 | 629 | Baker | 13 | A | c, cr, d | 0.15 | 0.002 |
| B15 | m | 27 | 5.06 | 42.2 | 278 | Confectioner | 10 | A, RC | c, cr, d, g | 0.079 | 0.078 |
| B16 | f | 42 | 3.71 | 2.15 | 271 | Pizza | 12 | A, RC, U | g | 0.187 | 0.625 |
| B17 | m | 54 | 1.68 | <0.35 | 79.2 | Confectioner | 38 | A | hdm | 16 | n.d. |
| B18 | m | 59 | <0.35 | <0.35 | 673 | Baker-Confectioner | 22 | A, RC | n.k. | 0.23 | n.d. |
| B19 | m | 26 | 74.6 | 57.4 | 17.7 | Confectioner | 18 | A, RC | g | 1.16 | 0.15 |
| B20 | m | 43 | 13.8 | 11 | 538 | Baker | 19 | A | g, o | 0.25 | EAR |
| B21 | f | 34 | 2.05 | <0.35 | 229 | Confectioner | 2 | A | hdm, o | 0.5 | DAR |
| B22 | f | 41 | 1.77 | <0.35 | 23.4 | Cook/pastry maker | 1 | A | o | 0.23 | EAR |
| B23 | f | 53 | 0.41 | <0.35 | 469 | Homemaker | n.k. | n.k. | n.k. | n.d. | n.d. | m: male, f: female,
kUA/l: kilounit antigen per liter,
n.k.: not known,
A: Asthma, RC: Rhinoconjunctivitis, U: Urticaria,
c: cat, cr: cockroach, d: dog, g: grass pollen, h: horse, hdm: house dust mite, m: molds, o: olive pollen,
PC20: Methochaline inhalation challenge (positive if <16 mg/ml),
SIC: specific inhalation challenge,
EAR: early asthmatic response, DAR: dual asthmatic response, LAR: late asthmatic response,
n.d.: not done

TABLE VIII

Demographic, clinical and serological characteristics of patients suffering from food

| Patient | Sex | Age | Wheat flour IgE kUA/l | *Phleum pratense* IgE kUA/l | Total IgE kU/l | Symptoms | DBPCFC | Other allergies |
|---|---|---|---|---|---|---|---|---|
| F1 | f | 56 | 0.74 | <0.35 | 820 | U | n.d. | s |
| F2 | f | 50 | 0.78 | <0.35 | 275 | Ab, CJ, Di, P | n.d. | hdm |
| F3 | f | 49 | >100 | 0.65 | 1794 | no symtoms-diet | n.d. | g, hdm, n, sh |
| F4 | f | 72 | 5.99 | <0.35 | 325 | E, D, P | n.d. | he, n, s |
| F5 | f | 11 | 2.15 | 3.28 | 11 | A, C, Ri | n.d. | g, n, s, o |
| F6 | f | 40 | 1.9 | <0.35 | 19.3 | C, CJ, S | n.d. | n.k. |
| F7 | m | 11 | 0.92 | 1.21 | 118 | n.k. | n.d. | g, n, s |
| F8 | m | 24 | 5.76 | <0.35 | 111 | C, CJ, N, R | n.d. | n.k. |
| F9 | f | 21 | 1.22 | 25.8 | 94.6 | C, N, P, R | n.d. | g |
| F10 | f | 5 | 1.93 | 34.3 | 453 | RC | n.d. | a, b, cm, g, n |
| F11 | f | 29 | 1.55 | 10.4 | 101 | De, Ri | n.d. | c, b, g, p |
| F12 | f | 45 | 5.72 | 1.12 | 30.1 | A, C, D, blisters on tongue | n.d. | g, n, s, r |
| F13 | m | 7 | 2.8 | >100 | <2000 | B, RC | n.d. | a, b, g |
| F14 | f | 1 | 0.81 | n.d. | 46.3 | n.k. | n.d. | cm, he |
| F15 | f | 28 | 1.27 | >100 | 616 | n.k. | n.d. | a, cm, g, l, m |
| F16 | m | 50 | 7.57 | 22.6 | 450 | A, C, D, N, RC | n.d. | b, g |
| F17 | f | 51 | 3.97 | 5.12 | 44.1 | Di, F | n.d. | f, g, n |
| F18 | f | 43 | 1.03 | 58.3 | 338 | C | n.d. | b, g, h, n, s |

TABLE VIII-continued

Demographic, clinical and serological characteristics of patients suffering from food

| Patient | Sex | Age | Wheat flour IgE kUA/l | *Phleum pratense* IgE kUA/l | Total IgE kU/l | Symptoms | DBPCFC | Other allergies |
|---|---|---|---|---|---|---|---|---|
| F19 | f | 19 | 20.5 | <0.35 | 949 | A, C, D, R | n.d. | n.k. |
| F20 | f | 57 | 17.6 | <0.35 | 174 | n.k. | n.d. | n.k. |
| F21 | m | 12 | 0.81 | 1.47 | 769 | A, RC | n.d. | he, g, w |
| F22 | f | 55 | 2.11 | <0.35 | 152 | no symtoms-diet | n.d. | n, sea |
| F23 | m | 43 | 4.24 | 2.41 | 207 | n.k. | n.d. | n.k. |
| F24 | f | 33 | 1.65 | <0.35 | 253 | n.k. | n.d. | n.k. |
| F25 | m | 51 | 1.64 | >100 | 45 | n.k. | n.d. | n.k. |
| F26 | m | 27 | 6.11 | 67.7 | 974 | C, CJ, D, Ri, in the past A | n.d. | ca, he, g, ce, sp |
| F27 | f | 9 | 6.47 | >100 | 1233.5 | E, Ri | + | n.k. |
| F28 | m | 0.5 | 7.39 | <0.35 | 65.2 | E, U, Wheezing | + | n.k. |
| F29 | f | 1 | 33.5 | <0.35 | 201 | Redness, itching | + | cm, he |
| F30 | f | 1 | 10 | n.d. | 25.5 | U, itching | + | cm, he, s |
| F31 | m | 1 | 18.6 | n.d. | 1343 | U | + | s |
| F32 | m | 1 | 35.1 | 0.83 | 325 | U, Ri, itching | + | g, s |
| F33 | f | 1 | 4.27 | <0.35 | 38.4 | U, Ri, Redness | + | n.k. |
| F34 | f | 0.5 | 21.3 | <0.35 | 1511 | U | + | cm |
| F35 | f | 1 | 5.21 | n.d. | 1718 | AD, G, U | + | cm |
| F36 | m | 1 | 61.4 | 0.69 | 876 | Redness, itching | + | g, cm |
| F37 | m | 1 | 52 | 0.38 | 254 | Ri, U | + | cm, he, g |
| F38 | f | 0.5 | 94.4 | 1.9 | 1524 | De, Ri, | open challenge, + | n.k. | m: male, f: female, n.k.: not known, n.d.: not done, kUA/l: kilounit antigen per liter, A: Asthma, Ab: Abdominaigia, B: Bronchitis, C: Cough, CJ: Conjunctivitis, D: Dyspnea, De: Dermatitis, Di: Diahmoe, E: Eczema, F: Flatulence, G: Gastro-intestinal symptoms, N: Nasal congestion, P: Pruritus, R: Rhinorrhoe, RC: Rhinoconjunctivitis, Ri: Rhinitis, S: Sore throat, U: Urticaria, V: Vertigo, Vo: Vomiting, DBPCFC: double blind placebo controlled food challenge, a: artsmisia, b: birch pollen, o: oat, ca: caroites, cm: cows milk, f: formaldehyd, g: grass pollen, h: hazelnut, he: hens egg, hdm: house dust mite, l: latex, m: malt, n: nuts, o: orange, p: plum, r: rice, s: soybean, ce: celery, sea: seafood, sh: shrimps, sp: spices, w: wesp

TABLE IX

Demographic, clinical and serological characteristics of patients suffering from grass

| Patient | Sex | Age | *Phleum pratense* IgE kUA/l | Wheat flour IgE kUA/l | Total IgE kU/l | Symptoms | Other allergies |
|---|---|---|---|---|---|---|---|
| G1 | m | 22 | 37.8 | 1.13 | 529 | D, RC, U | c, b, d, hdm, s |
| G2 | m | 30 | 44.6 | 0.52 | 290 | D, RC | b, a, hdm, d |
| G3 | f | 25 | 59.8 | <0.35 | 1004 | RC | b, d, hdm, h, ce |
| G4 | m | n.k. | 25.9 | 3.62 | 140 | RC | a, b |
| G5 | f | 22 | 37.2 | <0.35 | 566 | R | b, c, hdm |
| G6 | f | 22 | 22.4 | <0.35 | 77.4 | RC | hdm, r |
| G7 | m | 24 | 30.8 | <0.35 | 60.8 | n.k. | n.k. |
| G8 | m | 35 | 9.92 | <0.35 | 88.8 | D | b |
| G9 | m | 36 | 20.7 | 0.45 | 128 | R | ap, b, hdm |
| G10 | f | 22 | >100 | 4.13 | >5000 | RC | b, c, hdm, rye |
| G11 | m | 41 | 49.3 | 4.01 | >2000 | A, CJ | a, b, c, hdm |
| G12 | m | 37 | n.d. | 1.11 | 243 | n.k. | n.k. |
| G13 | m | 28 | 39.3 | 1.06 | 144 | RC | b, a |
| G14 | f | 27 | >100 | <0.35 | 260 | A, RC | n.k. |
| G15 | m | 39 | >100 | 11.1 | 401 | n.k. | n.k. |
| G16 | m | 54 | >100 | 9.93 | 1528 | A, CJ | n.k. |
| G17 | m | 45 | n.d. | 1.76 | 175 | RC | d, hdm, s, p | m: male, f: female, n.k.: not known, n.d.: not done, kUA/l: kilounit antigen per liter, A: Asthma, CJ: Conjunctivitis, D: Dyspnea, RC: Rhinoconjunctivitis, R: Rhinitis, U: Urticaria, a: artemisia, ap: apple, b: birch pollen, c: cat, d: dog, h: hazelnut, hdm: house dust mite, r: rabbit, s: soybean, ce: celery, p: potato

REFERENCES

1. Quirce, S., M. Fernandez-Nieto, C. Escudero, J. Cuesta, M. de Las Heras, and J. Sastre. 2006. Bronchial responsiveness to bakery-derived allergens is strongly dependent on specific skin sensitivity. *Allergy* 61:1202-1208.
2. Constantin, C., W. D. Huber, G. Granditsch, M. Weghofer, and R. Valenta. 2005. Different profiles of wheat antigens are recognised by patients suffering from coeliac disease and IgE-mediated food allergy. *Int Arch Allergy Immunol* 138:257-266.
3. Yeh, K., R. Juang, and J. Su. 1991. A rapid and efficient method for a RNA isolation from plants with high carbohydrate content. *Focus* 13:102-103.
4. Sambrook, J., E. F. Fritsch, and T. Maniatis. 1989. *Molecular Cloning: A laboratory Manual*. Cold Spring Harbor Laboratory Press.
5. Breiteneder, H., K. Pettenburger, A. Bito, R. Valenta, D. Kraft, H. Rumpold, O, Scheiner, and M. Breitenbach. 1989. The gene coding for the major birch pollen allergen Bet v 1, is highly homologous to a pea disease resistance response gene. *Embo J* 8:1935-1938.
6. Stern, D. A., J. Riedler, D. Nowak, C. Braun-Fahrlander, I. Swoboda, N. Balic, K. W. Chen, S. Vrtala, H. Gronlund, M. van Hage, R. Valenta, S. Spitzauer, E. Von Mutius, and D. Vercelli. 2007. Exposure to a farming environment has allergen-specific protective effects on TH2-dependent isotype switching in response to common inhalants. *J Allergy Clin Immunol* 119:351-358.
7. Laemmli, U. K. 1970. Cleavage of structural proteins during the assembly of the head of bacteriophage T4. *Nature* 227:680-685.
8. Towbin, H., T. Staehelin, and J. Gordon. 1979. Electrophoretic transfer of proteins from polyacrylamide gels to nitrocellulose sheets: procedure and some applications. *Proc Natl Acad Sci USA* 76:4350-4354.
9. Whitmore, L., and B. A. Wallace. 2004. DICHROWEB, an online server for protein secondary structure analyses from circular dichroism spectroscopic data. *Nucleic Acids Res* 32:W668-673.
10. Kaul, S., D. Luttkopf, B. Kastner, L. Vogel, G. Holtz, S. Vieths, and A. Hoffmann. 2007. Mediator release assays based on human or murine immunoglobulin E in allergen standardization. *Clin Exp Allergy* 37:141-150.
11. Richardson, M., and L. Cossins. 1974. Chymotryptic inhibitor I from potatoes: the amino acid sequences of subunits B, C, and D. *FEBS Lett* 45:11-13.
12. Vrtala S, Fischer S, Grote M, Vangelista L, Pastore A, Sperr W R, et al. 1999. Molecular, immunological, and structural characterization of Phl p 6, a major allergen and P-particle-associated protein from Timothy grass (*Phleum pratense*) pollen. *J Immunol* 163:5489-96.
13. Nystrand M. 2006. A multiplexed immunoassay for the rapid detection of specific IgE in allergy diagnosis. *IVDT* 2006:61.
14. Nilsson K, Bennich H, Johansson S G, Ponten J. 1970. Established immunoglobulin producing myeloma (IgE) and lymphoblastoid (IgG) cell lines from an IgE myeloma patient. *Clin Exp Immunol* 7:477-89.
15. Constantin C, Quirce S, Grote M, Touraev A, Swoboda I, Stoecklinger A, et al. Molecular and immunological characterization of a wheat serine proteinase-inhibitor as a novel allergen in baker's asthma. Unpublished.
16. Laffer S, Valenta R, Vrtala S, Susani M, van Ree R, Kraft D, et al. 1994. Complementary DNA cloning of the major allergen Phl p I from timothy grass (*Phleum pratense*); recombinant Phl p I inhibits IgE binding to group I allergens from eight different grass species. *J Allergy Clin Immunol* 94:689-98.
17. Vrtala S, Sperr W R, Reimitzer I, van Ree R, Laffer S, Muller W D, et al. 1993. cDNA cloning of a major allergen from timothy grass (*Phleum pratense*) pollen; characterization of the recombinant Phl pV allergen. *J Immunol* 151:4773-81.
18. Niederberger V, Hayek B, Vrtala S, Laffer S, Twardosz A, Vangelista L, et al. 1999, Calcium-dependent immunoglobulin E recognition of the apo- and calcium-bound form of a cross-reactive two EF-hand timothy grass pollen allergen, Phl p 7. *Faseb J* 13:843-56.
19. Valenta R, Ball T, Vrtala S, Duchene M, Kraft D, Scheiner 0. 1994. cDNA cloning and expression of timothy grass (*Phleum pratense*) pollen profilin in *Escherichia coli*: comparison with birch pollen profilin. *Biochem Biophys Res Commun* 199:106-18.
20. Kazemi-Shirazi L, Niederberger V, Linhart B, Lidholm J, Kraft D, Valenta R. 2002. Recombinant marker allergens: diagnostic gatekeepers for the treatment of allergy. *Int Arch Allergy Immunol* 127:259-68.
21. Andersson K, Lidholm J. 2003. Characteristics and immunobiology of grass pollen allergens. *Int Arch Allergy Immunol* 130:87-107.
22. Sampson H A. 1999. Food allergy. Part 2: diagnosis and management. *J Allergy Clin Immunol* 103:981-9.
23. Radauer C, Willerroider M, Fuchs H, Hoffmann-Sommergruber K, Thalhamer J, Ferreira F, et al. 2006. Cross-reactive and species-specific immunoglobulin E epitopes of plant profilins: an experimental and structure-based analysis. *Clin Exp Allergy* 36:920-9.

The invention claimed is:

1. A diagnostic kit for performing a method for in vitro diagnosis of IgE-mediated allergy, comprising an isolated polypeptide having the amino acid sequence according to SEQ ID NO: 2, 4, 6, 8 or 10, wherein the polypeptide is bound to a solid support.

2. The kit according to claim 1 wherein the solid support is a nitrocellulose membrane or a microarray.

3. The kit according to claim 1, wherein the polypeptide has the amino acid sequence according to SEQ ID NO: 2.

* * * * *

SEQUENCE LISTING

```
<160> NUMBER OF SEQ ID NOS: 10

<210> SEQ ID NO 1
<211> LENGTH: 418
<212> TYPE: DNA
<213> ORGANISM: Triticum aestivum
<220> FEATURE:
<221> NAME/KEY: CDS
<222> LOCATION: (1)..(252)
<223> OTHER INFORMATION: Clone 10

<400> SEQUENCE: 1 atg agc cct gtg gtg aag aag ccg gag gga ggg aac acc gat act ggt      48
Met Ser Pro Val Val Lys Lys Pro Glu Gly Gly Asn Thr Asp Thr Gly
1               5                   10                  15 gac cat cac aac cag aag acg gag tgg cca gag ttg gtg ggg aag tcg      96
Asp His His Asn Gln Lys Thr Glu Trp Pro Glu Leu Val Gly Lys Ser
```

```
                    20                  25                  30
gtg gag gag gcc aag aag gtg att atg cag gac aag tca gag gca cag        144
Val Glu Glu Ala Lys Lys Val Ile Met Gln Asp Lys Ser Glu Ala Gln
            35                  40                  45 atc gta gtt cta ccg gtg ggg aca att gtg acc atg gaa tat cga atc        192
Ile Val Val Leu Pro Val Gly Thr Ile Val Thr Met Glu Tyr Arg Ile
 50                  55                  60 gac cgt gtc cgc ctc ttt gtt gac agt ctc gac aaa att gcc cag gtc        240
Asp Arg Val Arg Leu Phe Val Asp Ser Leu Asp Lys Ile Ala Gln Val
65                  70                  75                  80 ccc agg gtc ggc tagcaagctt aagatctagc ctgctcctag cgtatatgta            292
Pro Arg Val Gly tcgtggcttg ataatctctt cttggatata gcaagattga gatatataga tcatatacaa     352
taagagttga tgcatggaaa gtgaatggat aatagaataa gtcagagagc gcgtaaaaaa     412
aaaaaa                                                                 418

<210> SEQ ID NO 2
<211> LENGTH: 84
<212> TYPE: PRT
<213> ORGANISM: Triticum aestivum

<400> SEQUENCE: 2

Met Ser Pro Val Val Lys Lys Pro Glu Gly Gly Asn Thr Asp Thr Gly
1               5                   10                  15

Asp His His Asn Gln Lys Thr Glu Trp Pro Glu Leu Val Gly Lys Ser
            20                  25                  30

Val Glu Glu Ala Lys Lys Val Ile Met Gln Asp Lys Ser Glu Ala Gln
        35                  40                  45

Ile Val Val Leu Pro Val Gly Thr Ile Val Thr Met Glu Tyr Arg Ile
    50                  55                  60

Asp Arg Val Arg Leu Phe Val Asp Ser Leu Asp Lys Ile Ala Gln Val
65                  70                  75                  80

Pro Arg Val Gly

<210> SEQ ID NO 3
<211> LENGTH: 755
<212> TYPE: DNA
<213> ORGANISM: Triticum aestivum
<220> FEATURE:
<221> NAME/KEY: CDS
<222> LOCATION: (49)..(402)
<223> OTHER INFORMATION: Clone 37

<400> SEQUENCE: 3
ccgcgcacgc accaaaatca ccttcgatct catcaccggg gaaggggg atg gcc gcc         57
                                                    Met Ala Ala
                                                      1 gag gag gga gcc gtg ata gcg tgc cac acc aag caa gag ttc gac acc        105
Glu Glu Gly Ala Val Ile Ala Cys His Thr Lys Gln Glu Phe Asp Thr
     5                  10                  15 cac atg gct aat ggc aag gag acc ggc aag ctg gtg atc att gac ttc        153
His Met Ala Asn Gly Lys Glu Thr Gly Lys Leu Val Ile Ile Asp Phe
20                  25                  30                  35 act gct tcc tgg tgc ggt cct tgt cgt gtc ata gcc cca gtc ttt gct        201
Thr Ala Ser Trp Cys Gly Pro Cys Arg Val Ile Ala Pro Val Phe Ala
            40                  45                  50 gag tac gcc aag aag ttc cct ggc gcc att ttc ctg aag gtg gac gtt        249
Glu Tyr Ala Lys Lys Phe Pro Gly Ala Ile Phe Leu Lys Val Asp Val
        55                  60                  65
```

```
gac gag ctg aag gac gtc gct gaa gca tac aac gtt gag gca atg ccg      297
Asp Glu Leu Lys Asp Val Ala Glu Ala Tyr Asn Val Glu Ala Met Pro
            70                  75                  80 acc ttc ctg ttt atc aag gat ggt gcg aag gtg gac act gtt gtc ggt      345
Thr Phe Leu Phe Ile Lys Asp Gly Ala Lys Val Asp Thr Val Val Gly
     85                  90                  95 ggc agg aag gat gat atc cat acc aag ata gtg gcc ctc atg ggt tct      393
Gly Arg Lys Asp Asp Ile His Thr Lys Ile Val Ala Leu Met Gly Ser
100                 105                 110                 115 gca tct gcc taagaaggga agagtgatgc ccctcttgtg tcaataagag              442
Ala Ser Ala ccagcacctg gtgtaagtag ttatcgctgc agtatgcttt ggcttagtcg tgactgaact    502
ttgtgatgat tcggtttaga gttcagaact tcagacattt gcaccggttg ttctgaatta    562
cagtacctaa tgttttgcta cagttgcttc gttgtgaagt ttggataact atcctgtctg    622
aatgttaatg caaagccaat atgccgctga cggaattcca agctgagcgc cggtcgctac    682
cattaccagt tggtctggtg tcaacgggat ccgcgaatca cgaattctgg atccgatacg    742
taacgcgtct gca                                                      755

<210> SEQ ID NO 4
<211> LENGTH: 118
<212> TYPE: PRT
<213> ORGANISM: Triticum aestivum

<400> SEQUENCE: 4

Met Ala Ala Glu Glu Gly Ala Val Ile Ala Cys His Thr Lys Gln Glu
1               5                   10                  15

Phe Asp Thr His Met Ala Asn Gly Lys Glu Thr Gly Lys Leu Val Ile
            20                  25                  30

Ile Asp Phe Thr Ala Ser Trp Cys Gly Pro Cys Arg Val Ile Ala Pro
        35                  40                  45

Val Phe Ala Glu Tyr Ala Lys Lys Phe Pro Gly Ala Ile Phe Leu Lys
    50                  55                  60

Val Asp Val Asp Glu Leu Lys Asp Val Ala Glu Ala Tyr Asn Val Glu
65                  70                  75                  80

Ala Met Pro Thr Phe Leu Phe Ile Lys Asp Gly Ala Lys Val Asp Thr
                85                  90                  95

Val Val Gly Gly Arg Lys Asp Asp Ile His Thr Lys Ile Val Ala Leu
            100                 105                 110

Met Gly Ser Ala Ser Ala
        115

<210> SEQ ID NO 5
<211> LENGTH: 854
<212> TYPE: DNA
<213> ORGANISM: Triticum aestivum
<220> FEATURE:
<221> NAME/KEY: CDS
<222> LOCATION: (55)..(720)
<223> OTHER INFORMATION: Clone 38

<400> SEQUENCE: 5
cggaattccc aaacacaaac acagatcgat cgagatccag agcaaccagg agca atg      57
                                                              Met
                                                              1 gcg ggc gag aag ggc ctg gtg ctg ctg gac ttc tgg gtg agc ccg ttc     105
Ala Gly Glu Lys Gly Leu Val Leu Leu Asp Phe Trp Val Ser Pro Phe
        5                   10                  15
```

```
ggg cag cgc gtc cgc atc gcg ctg gcg gag aag ggc ctg ccc tac gag    153
Gly Gln Arg Val Arg Ile Ala Leu Ala Glu Lys Gly Leu Pro Tyr Glu
         20                  25                  30 tac gcg gag gag gac ctg atg gcc ggc aag agc gac cgc ctc ctc cgc    201
Tyr Ala Glu Glu Asp Leu Met Ala Gly Lys Ser Asp Arg Leu Leu Arg
 35                  40                  45 gcc aac ccg gtg cac aag aag atc ccg gtg ctc ctc cac gac ggc cgc    249
Ala Asn Pro Val His Lys Lys Ile Pro Val Leu Leu His Asp Gly Arg
50                  55                  60                  65 ccc gtc aac gag tcc ctc atc atc ctc cag tac ctg gag gac gcc ttc    297
Pro Val Asn Glu Ser Leu Ile Ile Leu Gln Tyr Leu Glu Asp Ala Phe
                 70                  75                  80 ccg gac gcc ccg gca ctg ctc ccc tcc gac ccc tac gcg cgc gcg cag    345
Pro Asp Ala Pro Ala Leu Leu Pro Ser Asp Pro Tyr Ala Arg Ala Gln
             85                  90                  95 gcc cgc ttc tgg gcc gac tac gtc gac aag aag gtc tac gac tgc ggc    393
Ala Arg Phe Trp Ala Asp Tyr Val Asp Lys Lys Val Tyr Asp Cys Gly
        100                 105                 110 tcc cgc ctc tgg aag ctc aag ggc gag ccg cag gcg cag gcg cgc gcc    441
Ser Arg Leu Trp Lys Leu Lys Gly Glu Pro Gln Ala Gln Ala Arg Ala
    115                 120                 125 gag atg ctg gac atc ctc aag acc ctc gac ggc gcg ctc ggg gac aag    489
Glu Met Leu Asp Ile Leu Lys Thr Leu Asp Gly Ala Leu Gly Asp Lys
130                 135                 140                 145 ccc ttc ttc ggc ggc gac aag ttc ggg ttc gtc gac gcc gcc ttc gcg    537
Pro Phe Phe Gly Gly Asp Lys Phe Gly Phe Val Asp Ala Ala Phe Ala
                150                 155                 160 ccc ttc acc gcg tgg ttc cac agc tac gag agg tac ggc gag ttc agc    585
Pro Phe Thr Ala Trp Phe His Ser Tyr Glu Arg Tyr Gly Glu Phe Ser
            165                 170                 175 ctg ccg gag gtg gcg ccc aag atc gcg gcg tgg gcc aag cgc tgc ggc    633
Leu Pro Glu Val Ala Pro Lys Ile Ala Ala Trp Ala Lys Arg Cys Gly
        180                 185                 190 gag cgg gag agc gtc gcc aag agc ctc tac tcg ccg gac aag gtg tac    681
Glu Arg Glu Ser Val Ala Lys Ser Leu Tyr Ser Pro Asp Lys Val Tyr
    195                 200                 205 gac ttc atc ggc ctg ctc aag aag aag tac ggc atc gag tagccgcgcg     730
Asp Phe Ile Gly Leu Leu Lys Lys Lys Tyr Gly Ile Glu
210                 215                 220 gacggacggg cggccatgca tgcgccatcc cgccggccgg ccaataaatc agggagcgtt    790
tgggtggccc tacagtgcgt acgtttcgga tattgatttc ttcgtggagt ctagtgttcg    850
tgcg                                                                 854

<210> SEQ ID NO 6
<211> LENGTH: 222
<212> TYPE: PRT
<213> ORGANISM: Triticum aestivum

<400> SEQUENCE: 6

Met Ala Gly Glu Lys Gly Leu Val Leu Leu Asp Phe Trp Val Ser Pro
 1               5                   10                  15

Phe Gly Gln Arg Val Arg Ile Ala Leu Ala Glu Lys Gly Leu Pro Tyr
             20                  25                  30

Glu Tyr Ala Glu Glu Asp Leu Met Ala Gly Lys Ser Asp Arg Leu Leu
         35                  40                  45

Arg Ala Asn Pro Val His Lys Lys Ile Pro Val Leu Leu His Asp Gly
     50                  55                  60
```

```
Arg Pro Val Asn Glu Ser Leu Ile Ile Leu Gln Tyr Leu Glu Asp Ala
 65                  70                  75                  80

Phe Pro Asp Ala Pro Ala Leu Leu Pro Ser Pro Tyr Ala Arg Ala
                 85                  90                  95

Gln Ala Arg Phe Trp Ala Asp Tyr Val Asp Lys Lys Val Tyr Asp Cys
                100                 105                 110

Gly Ser Arg Leu Trp Lys Leu Lys Gly Glu Pro Gln Ala Gln Ala Arg
                115                 120                 125

Ala Glu Met Leu Asp Ile Leu Lys Thr Leu Asp Gly Ala Leu Gly Asp
130                 135                 140

Lys Pro Phe Phe Gly Gly Asp Lys Phe Gly Phe Val Asp Ala Ala Phe
145                 150                 155                 160

Ala Pro Phe Thr Ala Trp Phe His Ser Tyr Glu Arg Tyr Gly Glu Phe
                165                 170                 175

Ser Leu Pro Glu Val Ala Pro Lys Ile Ala Ala Trp Ala Lys Arg Cys
                180                 185                 190

Gly Glu Arg Glu Ser Val Ala Lys Ser Leu Tyr Ser Pro Asp Lys Val
                195                 200                 205

Tyr Asp Phe Ile Gly Leu Leu Lys Lys Lys Tyr Gly Ile Glu
                210                 215                 220

<210> SEQ ID NO 7
<211> LENGTH: 891
<212> TYPE: DNA
<213> ORGANISM: Triticum aestivum
<220> FEATURE:
<221> NAME/KEY: CDS
<222> LOCATION: (1)..(654)
<223> OTHER INFORMATION: Clone 112

<400> SEQUENCE: 7 atg ccg ggc ctc acc atc ggc gac acc gtc ccc aac ctg gag ctg gac      48
Met Pro Gly Leu Thr Ile Gly Asp Thr Val Pro Asn Leu Glu Leu Asp
1               5                   10                  15 tcc acc cat ggc aag atc cgc atc cac gac tac gtc ggc aac ggc tac      96
Ser Thr His Gly Lys Ile Arg Ile His Asp Tyr Val Gly Asn Gly Tyr
                20                  25                  30 gtc atc ctc ttc tcc cac ccc ggt gat ttc acc ccg gtg tgc acg acg     144
Val Ile Leu Phe Ser His Pro Gly Asp Phe Thr Pro Val Cys Thr Thr
            35                  40                  45 gag ctg gcg gcc atg gcc aac tac gcc aag gag ttc gag aag cgg ggc     192
Glu Leu Ala Ala Met Ala Asn Tyr Ala Lys Glu Phe Glu Lys Arg Gly
        50                  55                  60 gtg aag ctg ctc ggc atc tcc tgc gac gac gtg cag tcc cac aag gag     240
Val Lys Leu Leu Gly Ile Ser Cys Asp Asp Val Gln Ser His Lys Glu
65                  70                  75                  80 tgg acc aag gac atc gag gcc tac aag cct ggg agc agg gtg acg tac     288
Trp Thr Lys Asp Ile Glu Ala Tyr Lys Pro Gly Ser Arg Val Thr Tyr
                85                  90                  95 ccg atc atg gcg gac ccg gac cgc tcc gcc atc aag cag ctc aac atg     336
Pro Ile Met Ala Asp Pro Asp Arg Ser Ala Ile Lys Gln Leu Asn Met
                100                 105                 110 gtc gac ccg gac gag aag gac ggc cag ggg cag ctg ccg tcc cgc acc     384
Val Asp Pro Asp Glu Lys Asp Gly Gln Gly Gln Leu Pro Ser Arg Thr
                115                 120                 125 ctg cac atc gtg ggg ccg gac aag gtg gtg aag ctg agc ttc ctg tac     432
Leu His Ile Val Gly Pro Asp Lys Val Val Lys Leu Ser Phe Leu Tyr
130                 135                 140 ccg tcg tgc acg ggg cgg aac atg gac gag gtg gtg cgg gcc gtg gac     480
Pro Ser Cys Thr Gly Arg Asn Met Asp Glu Val Val Arg Ala Val Asp
```

| | | | | | | | | | | | | | | |
|---|---|---|---|---|---|---|---|---|---|---|---|---|---|---|
| Pro | Ser | Cys | Thr | Gly | Arg | Asn | Met | Asp | Glu | Val | Val | Arg | Ala | Val | Asp |
| 145 | | | | 150 | | | | | 155 | | | | | 160 | |

```
tcg ctg ctg acg gcg gcc aag cac aag gtg gcc acc ccg gcc aac tgg    528
Ser Leu Leu Thr Ala Ala Lys His Lys Val Ala Thr Pro Ala Asn Trp
            165                 170                 175 aag ccc ggg gag tgc gtg gtg atc gcg ccc ggc gtc tcc gac gag gag    576
Lys Pro Gly Glu Cys Val Val Ile Ala Pro Gly Val Ser Asp Glu Glu
        180                 185                 190 gcc aag aag atg ttc ccg cag ggg ttc gag acc gcc gac ctg ccc tcc    624
Ala Lys Lys Met Phe Pro Gln Gly Phe Glu Thr Ala Asp Leu Pro Ser
                195                 200                 205 aag aag ggg tac ctc cgc ttc acc aag gtc taggcgtgcg cccgtgctag      674
Lys Lys Gly Tyr Leu Arg Phe Thr Lys Val
            210                 215 ctcgtccgcg cttgctcggt tacttcactt gtggcggtct tgtcatcgt ggtgcgtgcg   734 tactttgtg gtgctttatc tcgttcttc tgtaaatcta ctagcgtcgc cgagctatgt    794
atgtgtactg tgactttgt ctctttcatg tgtttcgatc gccggtgtat acatgggtgt   854
gtgttgggac tgttaaaaaa aaaaaaaaaa aaaaaaa                           891
```

<210> SEQ ID NO 8
<211> LENGTH: 218
<212> TYPE: PRT
<213> ORGANISM: Triticum aestivum

<400> SEQUENCE: 8

```
Met Pro Gly Leu Thr Ile Gly Asp Thr Val Pro Asn Leu Glu Leu Asp
1               5                   10                  15

Ser Thr His Gly Lys Ile Arg Ile His Asp Tyr Val Gly Asn Gly Tyr
            20                  25                  30

Val Ile Leu Phe Ser His Pro Gly Asp Phe Thr Pro Val Cys Thr Thr
        35                  40                  45

Glu Leu Ala Ala Met Ala Asn Tyr Ala Lys Glu Phe Glu Lys Arg Gly
    50                  55                  60

Val Lys Leu Leu Gly Ile Ser Cys Asp Asp Val Gln Ser His Lys Glu
65                  70                  75                  80

Trp Thr Lys Asp Ile Glu Ala Tyr Lys Pro Gly Ser Arg Val Thr Tyr
                85                  90                  95

Pro Ile Met Ala Asp Pro Asp Arg Ser Ala Ile Lys Gln Leu Asn Met
            100                 105                 110

Val Asp Pro Asp Glu Lys Asp Gly Gln Gly Gln Leu Pro Ser Arg Thr
        115                 120                 125

Leu His Ile Val Gly Pro Asp Lys Val Val Lys Leu Ser Phe Leu Tyr
    130                 135                 140

Pro Ser Cys Thr Gly Arg Asn Met Asp Glu Val Val Arg Ala Val Asp
145                 150                 155                 160

Ser Leu Leu Thr Ala Ala Lys His Lys Val Ala Thr Pro Ala Asn Trp
                165                 170                 175

Lys Pro Gly Glu Cys Val Val Ile Ala Pro Gly Val Ser Asp Glu Glu
            180                 185                 190

Ala Lys Lys Met Phe Pro Gln Gly Phe Glu Thr Ala Asp Leu Pro Ser
        195                 200                 205

Lys Lys Gly Tyr Leu Arg Phe Thr Lys Val
    210                 215
```

<210> SEQ ID NO 9

<211> LENGTH: 987
<212> TYPE: DNA
<213> ORGANISM: Triticum aestivum
<220> FEATURE:
<221> NAME/KEY: CDS
<222> LOCATION: (64)..(702)
<223> OTHER INFORMATION: Clone 126

<400> SEQUENCE: 9

```
ccttgcaagc caccgcccca aactgtgaaa ccccgtcaga aggaagcacc gtcgagagaa        60 gta atg gcg gac tac ggt gga gag tac ggg cac ccg tac ccg cgc gtc         108
    Met Ala Asp Tyr Gly Gly Glu Tyr Gly His Pro Tyr Pro Arg Val
    1               5                   10                  15 gac gag tac ggc aac cca gtg ccg ccg gtc gac cag tac ggc aac ccc         156
Asp Glu Tyr Gly Asn Pro Val Pro Pro Val Asp Gln Tyr Gly Asn Pro
                20                  25                  30 atc cca agg gaa ccg ggc cag gtt ccg gcg tac acc tcg ggg ggc gcc         204
Ile Pro Arg Glu Pro Gly Gln Val Pro Ala Tyr Thr Ser Gly Gly Ala
            35                  40                  45 gct ccg ccc tac agc tct gac ggc gcg ggc gcg gtg acg tcg gcc gac         252
Ala Pro Pro Tyr Ser Ser Asp Gly Ala Gly Ala Val Thr Ser Ala Asp
        50                  55                  60 tat gga gcg ggt gtc acg ccg ggc tac ggc ctg agc ggc gcc gtg cac         300
Tyr Gly Ala Gly Val Thr Pro Gly Tyr Gly Leu Ser Gly Ala Val His
65                  70                  75 ccg cag gag agc gtg gta ggc ggt gcc gtt ttc ccg tcc ggc acg gcg         348
Pro Gln Glu Ser Val Val Gly Gly Ala Val Phe Pro Ser Gly Thr Ala
80                  85                  90                  95 cac acg cac gag ggc gcg cta agc ggc agc ctc gcc cct ggc gag acc         396
His Thr His Glu Gly Ala Leu Ser Gly Ser Leu Ala Pro Gly Glu Thr
                100                 105                 110 acg gca tac gct tat gag ggc atg gtc ggc agt ggc atc ggc acc ggc         444
Thr Ala Tyr Ala Tyr Glu Gly Met Val Gly Ser Gly Ile Gly Thr Gly
            115                 120                 125 gac cag atc cag ccc acc aaa gag ggg cac acg acg ctg ggc gag act         492
Asp Gln Ile Gln Pro Thr Lys Glu Gly His Thr Thr Leu Gly Glu Thr
        130                 135                 140 ttg cgg cgc tcc tcc agc tct agc tcc agc tcg tcg tcc gag gat gac         540
Leu Arg Arg Ser Ser Ser Ser Ser Ser Ser Ser Ser Glu Asp Asp
    145                 150                 155 ggg caa ggc ggg agg cag agg aag aag aag agc atg aag gcg aag ata         588
Gly Gln Gly Gly Arg Gln Arg Lys Lys Lys Ser Met Lys Ala Lys Ile
160                 165                 170                 175 aag gag aaa ctc ccg ggc agc cac aag cag gag gag cac aag gcc ggg         636
Lys Glu Lys Leu Pro Gly Ser His Lys Gln Glu Glu His Lys Ala Gly
                180                 185                 190 cac acg gtg cca ccg gct ggg acg ggg acg cac gag aag atc aag gag         684
His Thr Val Pro Pro Ala Gly Thr Gly Thr His Glu Lys Ile Lys Glu
            195                 200                 205 aag ctc cct gga cac cac tgagcaacat caacatctgc ggcgcctcag                732
Lys Leu Pro Gly His His
        210 ttgacacgga attcgctttc ttggaccatg tacgacctaa attgtcactc gctgggtctg       792 taatgagctc gctatagcct tctgtacaat gattaagggt atttccttct gccttcttcg       852 tgtgtgtgat cggtgttgat agttgtatga gctagatttg gtgttgttcg tgttggtgta       912 tgcttagagc ctctttggga ctgctctgct tcgtaaaatt cagctccgct tcagaaaaaa       972 aaaaaaaaaa aaaaa                                                        987
```

```
<210> SEQ ID NO 10
<211> LENGTH: 213
<212> TYPE: PRT
<213> ORGANISM: Triticum aestivum

<400> SEQUENCE: 10

Met Ala Asp Tyr Gly Gly Glu Tyr Gly His Pro Tyr Pro Arg Val Asp
1               5                   10                  15

Glu Tyr Gly Asn Pro Val Pro Val Asp Gln Tyr Gly Asn Pro Ile
            20                  25                  30

Pro Arg Glu Pro Gly Gln Val Pro Ala Tyr Thr Ser Gly Ala Ala
        35                  40                  45

Pro Pro Tyr Ser Ser Asp Gly Ala Gly Ala Val Thr Ser Ala Asp Tyr
    50                  55                  60

Gly Ala Gly Val Thr Pro Gly Tyr Gly Leu Ser Gly Ala Val His Pro
65                  70                  75                  80

Gln Glu Ser Val Val Gly Gly Ala Val Phe Pro Ser Gly Thr Ala His
                85                  90                  95

Thr His Glu Gly Ala Leu Ser Gly Ser Leu Ala Pro Gly Glu Thr Thr
            100                 105                 110

Ala Tyr Ala Tyr Glu Gly Met Val Gly Ser Gly Ile Gly Thr Gly Asp
        115                 120                 125

Gln Ile Gln Pro Thr Lys Glu Gly His Thr Thr Leu Gly Glu Thr Leu
    130                 135                 140

Arg Arg Ser Ser Ser Ser Ser Ser Ser Ser Ser Glu Asp Asp Gly
145                 150                 155                 160

Gln Gly Gly Arg Gln Arg Lys Lys Lys Ser Met Lys Ala Lys Ile Lys
                165                 170                 175

Glu Lys Leu Pro Gly Ser His Lys Gln Glu Glu His Lys Ala Gly His
            180                 185                 190

Thr Val Pro Pro Ala Gly Thr Gly Thr His Glu Lys Ile Lys Glu Lys
        195                 200                 205

Leu Pro Gly His His
    210
```